(12) United States Patent
Oestergaard et al.

(10) Patent No.: US 9,458,446 B2
(45) Date of Patent: Oct. 4, 2016

(54) POLYPEPTIDES HAVING ENDOPEPTIDASE ACTIVITY AND POLYNUCLEOTIDES ENCODING SAME

(75) Inventors: Peter Rahbek Oestergaard, Virum (DK); Carsten P. Sonksen, Farum (DK); Tine Hoff, Holte (DK); Gitte B. Lynglev, Frederiksberg (DK)

(73) Assignee: NOVOZYMES A/S, Bagsvaerd (DK)

( * ) Notice: Subject to any disclaimer, the term of this patent is extended or adjusted under 35 U.S.C. 154(b) by 110 days.

(21) Appl. No.: 13/821,168

(22) PCT Filed: Sep. 30, 2011

(86) PCT No.: PCT/EP2011/067167
§ 371 (c)(1),
(2), (4) Date: Mar. 6, 2013

(87) PCT Pub. No.: WO2012/042037
PCT Pub. Date: Apr. 5, 2012

(65) Prior Publication Data
US 2013/0273203 A1      Oct. 17, 2013

Related U.S. Application Data

(60) Provisional application No. 61/423,641, filed on Dec. 16, 2010.

(30) Foreign Application Priority Data

Oct. 1, 2010 (EP) .................................... 10185793

(51) Int. Cl.
| C12N 9/52 | (2006.01) |
| C12P 21/06 | (2006.01) |
| A23J 3/34 | (2006.01) |
| A23L 1/305 | (2006.01) |

(52) U.S. Cl.
CPC .. *C12N 9/52* (2013.01); *A23J 3/34* (2013.01); *A23J 3/347* (2013.01); *A23L 1/3053* (2013.01); *C12P 21/06* (2013.01); *C12Y 302/00* (2013.01); *Y02P 20/52* (2015.11)

(58) Field of Classification Search
None
See application file for complete search history.

(56) References Cited

U.S. PATENT DOCUMENTS

| 5,039,532 A | 8/1991 | Jost et al. |
| 2008/0254505 A1* | 10/2008 | Budolfsen et al. .......... 435/68.1 |
| 2009/0155239 A1* | 6/2009 | Nakamura ................ 424/94.63 |

FOREIGN PATENT DOCUMENTS

| DK | WO 2009062942 A2 * | 5/2009 | ............... C07K 1/22 |
| WO | 93/04593 A1 | 3/1993 | |
| WO | 2009/101146 A1 | 8/2009 | |

OTHER PUBLICATIONS

UniProt Accession No. C6WDM8, Mar. 2010, 2 pages.*
Stackebrandt et al., Int. J. Sys. Bacteriol. 44:265-269, 1994.*
"Quick-Start Protocol" for QIAprep Spin Miniprep Kit, Oct. 2010, 2 pages.*
UniProt Accession No. W5WQZ3, Nov. 2015, 5 pages.*
Nagamine-Natsuka et al, J Biochem, vol. 118, No. 2, pp. 338-346 (1995).
Penas et al, Eur Food Res Technol, vol. 222, No. 3-4, pp. 286-29 (2006).
Spellman et al, Food Chem, vol. 114, No. 2, pp. 440-446 (2009).
Telishevskaya et al, 2000, Moscow 79.

* cited by examiner

*Primary Examiner* — David J Steadman
(74) *Attorney, Agent, or Firm* — Kristin McNamara

(57) ABSTRACT

The present invention relates to polypeptides having endopeptidase activity and to methods of producing and using the polypeptides. The invention also relates to methods of making a food protein hydrolysate using a trypsin-like endopeptidase derived from a bacterium.

14 Claims, 2 Drawing Sheets

US 9,458,446 B2

POLYPEPTIDES HAVING ENDOPEPTIDASE ACTIVITY AND POLYNUCLEOTIDES ENCODING SAME

CROSS-REFERENCE TO RELATED APPLICATIONS

This application is a 35 U.S.C. 371 national application of PCT/EP2011/067167 filed Sep. 30, 2011 which claims priority or the benefit under 35 U.S.C. 119 of European application no. 10185793.6 filed Oct. 1, 2010 and U.S. provisional application no. 61/423,641 filed Dec. 16, 2010 the contents of which are fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to polypeptides having endopeptidase activity and to methods of producing and using the polypeptides. The invention also relates to methods of making a protein hydrolysate such as a food protein hydrolysate.

2. Description of the Related Art

Trypsin (EC 3.4.21.4) is a serine protease found in the digestive system of many vertebrates, where it hydrolyses proteins. Trypsin cleaves peptide chains mainly at the carboxyl side of the amino acids lysine and arginine. Trypsin is available in high quantity in pancreas, and can be purified rather easily. Hence it has been used widely in various biotechnological processes. Trypsin is used in baby food to pre-digest it. It can break down the protein molecules, which helps the baby to digest it, as its stomach is not sufficiently developed to digest bigger protein molecules. Trypsin can be used to break down milk proteins to provide a partial milk protein hydrolysate for infant formulae. For example, WO93/04593 and U.S. Pat. No. 5,039,532 disclose use of pancreatic trypsin preparations for the production of hypoallergenic whey protein hydrolysates.

For several reasons, in the production of food and, in particular, in the production of baby food or infant formulae, use of proteolytic enzymes derived from a microorganism, such as a bacterium, may confer benefits. For example, production of bacterial enzymes can be easily optimized to be efficient and easy to control. Therefore, such enzymes can be produced in large quantities and at high purity. Also, use of a microbial enzyme will help overcoming increasing Quality Assurance related difficulties as regards extraction of enzymes from an animal source.

One object of the present invention has been to provide novel microbial proteases for potential use, e.g., in the food industry.

SUMMARY OF THE INVENTION

The present inventors have surprisingly found that a number of bacterial endopeptiadases have a cleavage specificity which is very similar to that of pancreatic trypsin. Further, such bacterial endopeptidases can be used to make food protein hydrolysates having similar properties, such as similar degree of hydrolysis and/or similar peptide spectra, as food protein hydrolysates obtained with pancreatic trypsin.

The inventors have further identified a novel bacterial endopeptidase which has trypsin-like activity.

The present invention therefore relates to isolated polypeptides having endopeptidase activity selected from the group consisting of:

(a) a polypeptide having at least 70% sequence identity to the mature polypeptide of SEQ ID NO: 2;

(b) a polypeptide encoded by a polynucleotide that hybridizes under low stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii);

(c) a polypeptide encoded by a polynucleotide having at least 70% sequence identity to the mature polypeptide coding sequence of SEQ ID NO: 1;

(d) a variant comprising a substitution, deletion, and/or insertion of one or more (several) amino acids of the mature polypeptide of SEQ ID NO: 2; and (e) a fragment of a polypeptide of (a), (b), (c) or (d) that has endopeptidase activity.

The present invention also relates to methods of producing the polypeptides.

The present invention also relates to methods of using the polypeptides for making a protein hydrolysate.

In another aspect, the present invention relates to a method of making a food protein hydrolysate comprising:

(a) providing a solution comprising food protein to be hydrolyzed;

(b) adding to said solution a trypsin-like endopeptidase derived from a bacterium; and (c) obtaining the food protein hydrolysate.

DEFINITIONS

Figure 1:
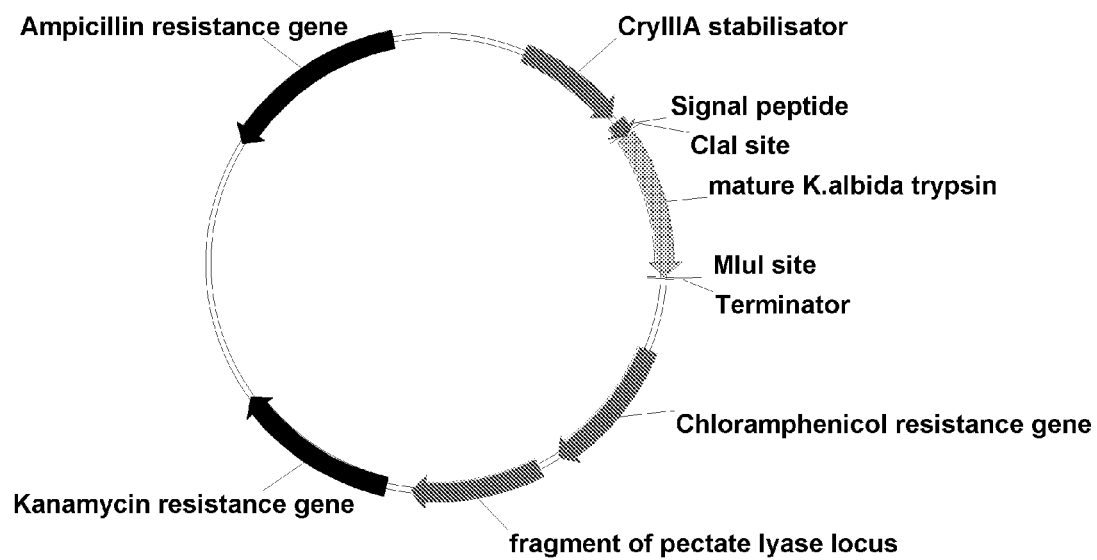
FIG. 1 shows a plasmid map of ExpVec8 with a gene encoding the trypsin-like endopeptidase from *Kutzneria albida*.

Endopeptidase activity: The term "endopeptidase activity" means a proteolytic activity, which is able to hydrolyse any peptide bond in a peptide. However, as endopeptidases often have catalytic sites involving binding to several amino acids and often on both sides of the cleavage point, endopeptidases in general have preference for non-terminal peptide bonds, in contrast to exopeptidases, which hydrolyse peptide bonds from either end of a peptide. Endopeptidases are normally classified as EC 3.4.21-25. For purposes of the present invention, endopeptidase activity may be determined by using the Protazyme AK assay as described in Example 2.

The polypeptides of the present invention may have at least 20%, e.g., at least 40%, at least 50%, at least 60%, at least 70%, at least 80%, at least 90%, at least 95%, or at least 100% of the endopeptidase activity of the mature polypeptide of SEQ ID NO: 2.

Trypsin-like endopeptidase: The term "trypsin-like endopeptidase" or "endopeptidase having a trypsin-like activity" is defined herein as an endopeptidase which preferentially cleaves peptides or proteins at the C-terminal side of the L-isomer of arginine and/or lysine. In a preferred embodiment, the trypsin-like endopeptidase preferentially cleaves peptides or proteins at the C-terminal side of arginine and lysine. This means that the endopeptidase has a higher specificity for cleaving after both of arginine and lysine than it has for cleaving after any other amino acid. In another preferred embodiment, the trypsin-like endopeptidase preferentially cleaves peptides or proteins at the C-terminal side of arginine or lysine. This means that the endopeptidase has a higher specificity for cleaving after any of arginine or lysine than it has for cleaving after any other amino acid. In another preferred embodiment, the trypsin-like endopeptidase preferentially cleaves peptides or proteins at the C-terminal side of arginine. This means that the endopeptidase has a higher specificity for cleaving after arginine than it has for cleaving after any other amino acid. In another preferred embodiment, the trypsin-like endopeptidase preferentially cleaves peptides or proteins at the C-terminal side of lysine. This means that the endopeptidase has a higher specificity for cleaving after lysine than it has for cleaving after any other amino acid.

Trypsin ratio: The "Trypsin ratio" is determined as the activity of the enzyme when cleaving after Arg or Lys (whichever is the larger) divided by the activity of the enzyme when cleaving after any one of Ala, Asp, Glu, Ile, Leu, Met, Phe or Val (whichever is the larger). In a preferred embodiment, a trypsin-like endopeptidase according to the invention has a Trypsin ratio of more than 100. I.e., in a preferred embodiment, a trypsin-like endopeptidase according to the invention has a specificity for cleaving after Arg or Lys (whichever is the larger) which is at least 100-fold higher than its specificity for cleaving after any one of Ala, Asp, Glu, Ile, Leu, Met, Phe or Val (whichever is the larger). Such activity measurements to determine the Trypsin ratio should be performed at a pH-value where the activity of the endopeptidase is at least half of the activity of the endopeptidase at its pH optimum. The Trypsin ratio may be determined as described in Example 2 of the present application.

Isolated polypeptide: The term "isolated polypeptide" means a polypeptide that is modified by the hand of man relative to that polypeptide as found in nature. In one embodiment, the polypeptide is at least 1% pure, e.g., at least 5% pure, at least 10% pure, at least 20% pure, at least 40% pure, at least 60% pure, at least 80% pure, or at least 90% pure, as determined by SDS-PAGE.

Substantially pure polypeptide: The term "substantially pure polypeptide" means a preparation that contains at most 10%, at most 8%, at most 6%, at most 5%, at most 4%, at most 3%, at most 2%, at most 1%, or preferably at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, or most preferably 100% pure by weight of the total polypeptide material present in the preparation. The polypeptides of the present invention are preferably in a substantially pure form. This can be accomplished, for example, by preparing the polypeptide by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one embodiment, the mature polypeptide is amino acids 1 to 225 of SEQ ID NO: 2 based on N-terminal sequencing and molecular weight determination as described in Example 2.

Mature polypeptide coding sequence: The term "mature polypeptide coding sequence" means a polynucleotide that encodes a mature polypeptide having endopeptidase activity. In one embodiment, the mature polypeptide coding sequence may be nucleotides 1 to 675 of SEQ ID NO: 1 based on the amino acid sequence of the mature polypeptide. In another embodiment, the mature polypeptide coding sequence may be nucleotides 82 to 756 of SEQ ID NO: 3.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 2.8.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Fragment: The term "fragment" means a polypeptide having one or more (several) amino acids deleted from the amino and/or carboxyl terminus of a mature polypeptide; wherein the fragment has endopeptidase activity. In one embodiment, a fragment contains at least 100 amino acid residues, at least 150 amino acid residues, or at least 200 amino acid residues.

Subsequence: The term "subsequence" means a polynucleotide having one or more (several) nucleotides deleted from the 5' and/or 3' end of a mature polypeptide coding sequence; wherein the subsequence encodes a fragment having endopeptidase activity. In one embodiment, a subsequence contains at least 300 nucleotides, e.g., at least 400 nucleotides, at least 500 nucleotides, or at least 600 nucleotides.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man relative to that polynucleotide as found in nature. In one embodiment, the isolated polynucleotide is at least 1% pure, e.g., at least 5% pure, preferably at least 10% pure, at least 20% pure, at least 40% pure, at least 60% pure, at least 80% pure, at least 90% pure, or more preferably at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, or at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, or at least 99.5% pure by weight. The polynucleotides of the present invention are preferably in a substantially pure form.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having endopeptidase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

DETAILED DESCRIPTION OF THE INVENTION

Polypeptides Having Endopeptidase Activity

Polypeptides

The present invention relates to isolated polypeptides having endopeptidase activity selected from the group consisting of:

(a) a polypeptide having at least 70% sequence identity to the mature polypeptide of SEQ ID NO: 2;

(b) a polypeptide encoded by a polynucleotide that hybridizes under low stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii);

(c) a polypeptide encoded by a polynucleotide having at least 70% sequence identity to the mature polypeptide coding sequence of SEQ ID NO: 1;

(d) a variant comprising a substitution, deletion, and/or insertion of one or more (several) amino acids of the mature polypeptide of SEQ ID NO: 2; and (e) a fragment of a polypeptide of (a), (b), (c) or (d) that has endopeptidase activity.

The present invention relates to isolated polypeptides having a sequence identity to the mature polypeptide of SEQ ID NO: 2 of at least 70%, at least 75%, at least 80%, at least 85%, at least 90%, at least 95%, at least 96%, at least 97%, at least 98%, at least 99%, or 100%, which have endopeptidase activity. In one embodiment, the polypeptides differ by no more than ten amino acids, e.g., by five amino acids, by four amino acids, by three amino acids, by two amino acids, or by one amino acid from the mature polypeptide of SEQ ID NO: 2.

A polypeptide of the present invention preferably comprises or consists of the amino acid sequence of SEQ ID NO: 2 or an allelic variant thereof; or is a fragment thereof having endopeptidase activity. In another embodiment, the polypeptide comprises or consists of the mature polypeptide of SEQ ID NO: 2. In another preferred embodiment, the polypeptide comprises or consists of amino acids 1 to 225 of SEQ ID NO: 2.

The present invention also relates to isolated polypeptides having endopeptidase activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1 or a subsequence thereof, as well as the amino acid sequence of SEQ ID NO: 2 or a fragment thereof, may be used to design nucleic acid probes to identify and clone DNA encoding polypeptides having endopeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides or at least 600 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having endopeptidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1; the genomic DNA sequence comprising the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In one embodiment, the nucleic acid probe is the mature polypeptide coding sequence of SEQ ID NO: 1. In another embodiment, the nucleic acid probe is nucleotides 1 to 200, nucleotides 201 to 400, nucleotides 401 to 600, or nucleotides 401 to 625 of SEQ ID NO: 1. In another embodiment, the nucleic acid probe is a polynucleotide that encodes the polypeptide of SEQ ID NO: 2 or a fragment thereof. In another preferred embodiment, the nucleic acid probe is SEQ ID NO: 1. In another embodiment, the nucleic acid probe is the polynucleotide contained in plasmid ExpVec8 which is contained in *E. coli* DSM 23706, wherein the polynucleotide encodes a polypeptide having endopeptidase activity. In another embodiment, the nucleic acid probe is the mature polypeptide coding region contained in plasmid ExpVec8 which is contained in *E. coli* DSM 23706.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated polypeptides having endopeptidase activity encoded by polynucleotides having a sequence identity to the mature polypeptide coding sequence of SEQ ID NO: 1 of at least 70%, at least 75%, at least 80%, at least 85%, at least 90%, at least 95%, at least 96%, at least 97%, at least 98%, at least 99%, or 100%.

The present invention also relates to variants comprising a substitution, deletion, and/or insertion of one or more (or several) amino acids of the mature polypeptide of SEQ ID NO: 2, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In. The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for endopeptidase activity, preferably trypsin-like endopeptidase activity, to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2 is not more than 10, e.g., 1, 2, 3, 4, 5, 6, 7, 8 or 9.

The polypeptide may be a hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Preferably, the polypeptides of the present invention are trypsin-like endopeptidases.

Sources of Polypeptides Having Endopeptidase Activity

A polypeptide having endopeptidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one embodiment, the polypeptide obtained from a given source is secreted extracellularly.

The polypeptide may be a bacterial polypeptide. For example, the polypeptide may be a gram-positive bacterial polypeptide such as an *Actinocynnema, Bacillus, Clostridium, Enterococcus, Geobacillus, Kribbella, Kutzneria, Lactobacillus, Lactococcus, Oceanobacillus, Staphylococcus, Streptococcus*, or *Streptomyces* polypeptide having endopeptidase activity, or a gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* polypeptide.

In one embodiment, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another embodiment, the polypeptide is a *Streptococcus equisimilis, Streptococcus pyogenes, Streptococcus uberis*, or *Streptococcus equi* subsp. *Zooepidemicus* polypeptide.

In another embodiment, the polypeptide is a *Streptomyces achromogenes, Streptomyces avermitilis, Streptomyces coelicolor, Streptomyces griseus*, or *Streptomyces lividans* polypeptide.

The polypeptide may also be a fungal polypeptide. For example, the polypeptide may be a yeast polypeptide such as a *Candida, Kluyveromyces, Pichia, Saccharomyces, Schizosaccharomyces*, or *Yarrowia* polypeptide; or a filamentous fungal polypeptide such as an *Acremonium, Agaricus, Alternaria, Aspergillus, Aureobasidium, Botryospaeria, Ceriporiopsis, Chaetomidium, Crysospotium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In another embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another embodiment, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* polypeptide.

In a preferred embodiment, the polypeptide is a *Kutzneria* polypeptide, e.g., a polypeptide obtained from *Kutzneria albida*, e.g., a polypeptide obtained from *Kutzneria albida* ATCC 25243 (obtainable from the ATCC culture collection).

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Nucleic Acid Constructs

The present invention also relates to nucleic acid constructs comprising a polynucleotide encoding a polypeptide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra. The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide encoding a polypeptide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a polypeptide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gramnegative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell. The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bactetiol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium* roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023 and Yelton et al., 1984, Proc. Natl. Acad. Sci. USA 81: 1470-1474. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred embodiment, the cell is of the genus Kutzneria. In a more preferred embodiment, the cell is Kutzneria albida. In a most preferred embodiment, the cell is Kutzneria albida ATCC 25243.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

In an alternative embodiment, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism Arabidopsis thaliana.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a polypeptide of the present invention. Preferably, the compositions are enriched in such a polypeptide. The term "enriched" indicates that the endopeptidase activity, preferably the trypsin-like endopeptidase activity, of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, or *Aspergillus oryzae*; *Fusarium*, e.g., *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, e.g., *Humicola insolens* or *Humicola lanuginosa*; or *Trichoderma*, e.g., *Trichoderma harzianum*, *Trichoderma koningii*, *Trichoderma longibrachiatum*, *Trichoderma reesei*, or *Trichoderma viride*.

The compositions may be prepared in accordance with methods known in the art and may be in the form of a liquid or a dry composition. For instance, the composition may be in the form of a granulate or a microgranulate. The polypeptide may be stabilized in accordance with methods known in the art.

Uses

The present invention is also directed to methods for using the polypeptides of the invention or compositions thereof.

Preferably, the invention relates to use of the polypeptides of the invention or compositions thereof for making a protein hydrolysate, preferably a food protein hydrolysate, more preferably a milk protein hydrolysate, e.g., a whey protein hydrolysate or a casein hydrolysate.

The invention also relates to a method of making a protein hydrolysate comprising:

(a) providing a solution comprising protein to be hydrolyzed;

(b) adding to said solution the polypeptide of the invention or a composition thereof; and (c) obtaining the protein hydrolysate.

In a preferred embodiment, the protein to be hydrolyzed is food protein and thus the protein hydrolysate obtained is a food protein hydrolysate.

The food protein may be any food protein. The solution comprising food protein may be a solution comprising protein material from a plant, such as, e.g., barley, canola, lupin, maize, oat, pea, potato, rice, soy, wheat, or any combination thereof. The solution comprising food protein may be a solution comprising protein material from an animal, such as, e.g., an egg protein material, a meat protein material or a milk protein material. It may also be a combination of plant-derived protein material(s) and animal-derived protein material(s).

In a preferred embodiment, the food protein is milk protein. I.e., the starting material is a solution comprising milk protein. Such solution may comprise whey protein and casein at any ratio, or it may comprise essentially only whey protein or essentially only casein, or it may be a solution of pure whey protein or pure casein. It may be, e.g., milk such as raw milk or any solution comprising milk protein derived from milk.

In one embodiment, such solution is a solution of whey protein, which may be sourced from whey obtained from cheese making, particularly a sweet whey such as that resulting from the coagulation of casein by rennet. The whey protein may also come from a whey protein concentrate or from a whey protein isolate. In a preferred embodiment, the milk protein is whey protein concentrate (WPC).

In another embodiment, such solution is a solution of casein. The source of the casein may be acid casein or non-fat milk solids.

The solution comprising food protein, such as the solution comprising milk protein, preferably comprises around 2-35% by weight of protein, more preferably around 5-30% by weight.

In one embodiment, the solution comprising milk protein, preferably the solution comprising whey protein, also comprises lactose.

It is to be understood that the solution may be in a form which may, technically speaking, rather be characterized as a dispersion.

The invention also relates to the use of the polypeptides of the invention for treatment of leather during wet processing, i.e. during soaking, dehairing and/or bating.

In a specific embodiment of the invention, the enzymatic treatment of leather with the polypeptides of the invention takes place during soaking. A soaking process of the present invention may be performed at conventional soaking conditions, i.e. a pH in the range pH 4-11, preferably the range pH 6-10, a temperature in the range 20-30° C., preferably the range 24-28° C., and a reaction time in the range 2-24 hours, preferably the range 4-16 hours, and together with known tensides and preservatives, if needed.

In a more specific embodiment of the invention, the enzymatic treatment of leather with the polypeptides of the invention takes place during dehairing. A dehairing process of the present invention may be performed at conventional conditions, i.e. a pH in the range of pH 5.5-12.5, preferably in the range of 6 to 12, more preferably in the range of 7 to 10, a temperature in the range of 5° C. to 32° C., preferably in the range of 15° C. to 30° C., and a reaction time of 1-5 hours, preferably between 1.5 and 4 hours.

In another specific embodiment, the enzymatic treatment of leather takes place during bating. In a most preferred embodiment, the enzymatic treatment takes place during bating, after the deliming phase. A bating process of the present invention may be performed at conventional conditions, i.e. a pH in the range pH 6-9, preferably the range pH 6.5-8.5, a temperature in the range 20-30° C., preferably the range 25-28° C., and a reaction time in the range 20-90 minutes, preferably the range 40-80 minutes.

Method of Making a Food Protein Hydrolysate

Method

In another aspect, the present invention relates to a method of making a food protein hydrolysate comprising:
(a) providing a solution comprising food protein to be hydrolyzed;
(b) adding to said solution a trypsin-like endopeptidase derived from a bacterium; and
(c) obtaining the food protein hydrolysate.

Food Protein Substrate

The food protein may be any food protein. The solution comprising food protein may be a solution comprising protein material from a plant, such as, e.g., barley, canola, lupin, maize, oat, pea, potato, rice, soy, wheat, or any combination thereof. The solution comprising food protein may be a solution comprising protein material from an animal, such as, e.g., an egg protein material, a meat protein material or a milk protein material. It may also be a combination of plant-derived protein material(s) and animal-derived protein material(s).

In a preferred embodiment, the food protein is milk protein, preferably whey protein. I.e., the starting material is a solution comprising milk protein. Such solution may comprise whey protein and casein at any ratio, or it may comprise essentially only whey protein or essentially only casein, or it may be a solution of pure whey protein or pure casein. It may be, e.g., raw milk or any solution comprising milk protein derived from raw milk.

In one embodiment, such solution is a solution of whey protein, which may be sourced from whey obtained from cheese making, particularly a sweet whey such as that resulting from the coagulation of casein by rennet. The whey protein may also come from a whey protein concentrate or from a whey protein isolate. In a preferred embodiment, the milk protein is whey protein concentrate (WPC).

In another embodiment, such solution is a solution of casein. The source of the casein may be acid casein or non-fat milk solids.

The solution comprising food protein, such as the solution comprising milk protein, preferably comprises around 2-35% by weight of protein, more preferably around 5-30% by weight, even more preferably around 5-20% by weight.

In one embodiment, the solution comprising milk protein, preferably the solution comprising whey protein, also comprises lactose.

It is to be understood that the solution may be in a form which may, technically speaking, rather be characterized as a dispersion.

Trypsin-Like Endopeptidase

The solution comprising food protein, such as the solution comprising milk protein, is treated with a trypsin-like endopeptidase derived from a bacterium.

For purposes of the present invention, the term "derived from" as used herein in connection with a polypeptide derived from a given source (i.e., a biological organism) may mean that the polypeptide is identical to or a variant of a polypeptide naturally encoded by the genome of that source, irrespective if the polypeptide is produced by another source, e.g., a strain in which a polynucleotide from the source encoding the endoprotease has been inserted.

The trypsin-like endopeptidase may be derived from a gram-positive bacterial strain such as a strain of *Actinosynnema*, *Bacillus*, *Clostridium*, *Enterococcus*, *Geobacillus*, *Kribbella*, *Kutzneria*, *Lactobacillus*, *Lactococcus*, *Oceanobacillus*, *Staphylococcus*, *Streptococcus*, or *Streptomyces*, or a gram-negative bacterial strain such as a strain of *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma*.

In one embodiment, the trypsin-like endopeptidase is derived from a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* strain.

In another embodiment, the trypsin-like endopeptidase is derived from a *Streptococcus equisimilis*, *Streptococcus pyogenes*, *Streptococcus uberis*, or *Streptococcus equi* subsp. *Zooepidemicus* strain.

In another embodiment, the trypsin-like endopeptidase is derived from a *Streptomyces achromogenes*, *Streptomyces avermitilis*, *Streptomyces coelicolor*, *Streptomyces griseus*, or *Streptomyces lividans* strain.

Such bacterial trypsin-like endopeptidase may have optimal proteolytic activity at a pH from about 5.0 to about 11.0, preferably at a pH from about 6 to about 10, and at a temperature from about 40° C. to about 75° C., preferably at a temperature from about 50° C. to about 70° C.

In a preferred embodiment, the trypsin-like endopeptidase has a sequence identity to the mature polypeptide of any of SEQ ID NOs: 2, 5 or 6 of at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%. In another preferred embodiment, the trypsin-like endopeptidase differs by no more than ten amino acids, e.g., by five amino acids, by four amino acids, by three amino acids, by two amino acids, or by one amino acid from the mature polypeptide of any of SEQ ID NOs: 2, 5 or 6.

The mature polypeptide of SEQ ID NO: 2 may be amino acids 1-225. The mature polypeptide of SEQ ID NO: 5 may be amino acids 38-261. The mature polypeptide of SEQ ID NO: 6 may be amino acids 40-266.

In a preferred embodiment, the trypsin-like endopeptidase is derived from an actinobacterium.

In a more preferred embodiment, the trypsin-like endopeptidase is derived from a strain of *Kutzneria*, e.g., from *Kutzneria albida*.

In another more preferred embodiment, the trypsin-like endopeptidase has a sequence identity to the mature polypeptide of SEQ ID NO: 2 of at least 70%, at least 75%, at least 80%, at least 85%, at least 90%, at least 95%, at least 96%, at least 97%, at least 98%, at least 99%, or 100%. In another preferred embodiment, the trypsin-like endopeptidase differs by no more than ten amino acids, e.g., by five amino acids, by four amino acids, by three amino acids, by two amino acids, or by one amino acid from the mature polypeptide of SEQ ID NO: 2. Such trypsin-like endopeptidase may have optimal proteolytic activity at a pH from about 5.0 to about 11.0, preferably at a pH from about 6 to about 10, and at a temperature from about 40° C. to about 75° C., preferably at a temperature from about 50° C. to about 70° C. It may be inhibited by aprotinin.

In another more preferred embodiment, the trypsin-like endopeptidase is derived from a strain of *Actinosynnema*, e.g., from *Actinosynnema mirum*. It may, e.g., have the amino acid sequence of the mature polypeptide of SEQ ID NO: 5 of the present application (UNIPROT:C6WDM8).

In another more preferred embodiment, the trypsin-like endopeptidase has a sequence identity to the mature polypeptide of SEQ ID NO: 5 of at least 70%, at least 75%, at least 80%, at least 85%, at least 90%, at least 95%, at least 96%, at least 97%, at least 98%, at least 99%, or 100%. In another preferred embodiment, the trypsin-like endopeptidase differs by no more than ten amino acids, e.g., by five amino acids, by four amino acids, by three amino acids, by two amino acids, or by one amino acid from the mature polypeptide of SEQ ID NO: 5. Such trypsin-like endopeptidase may have optimal proteolytic activity at a pH from about 5.0 to about 11.0, preferably at a pH from about 8 to about 10, and at a temperature from about 40° C. to about 75° C., preferably at a temperature from about 50° C. to about 70° C. It may be inhibited by PMSF.

In another more preferred embodiment, the trypsin-like endopeptidase is derived from a strain of *Kribbella*, e.g., from *Kribbella flavida*. It may, e.g., have the amino acid sequence of the mature polypeptide of SEQ ID NO: 6 of the present application (UNIPROT:D2PZJ1).

In another more preferred embodiment, the trypsin-like endopeptidase has a sequence identity to the mature polypeptide of SEQ ID NO: 6 of at least 70%, at least 75%, at least 80%, at least 85%, at least 90%, at least 95%, at least 96%, at least 97%, at least 98%, at least 99%, or 100%. In another preferred embodiment, the trypsin-like endopeptidase differs by no more than ten amino acids, e.g., by five amino acids, by four amino acids, by three amino acids, by two amino acids, or by one amino acid from the mature polypeptide of SEQ ID NO: 6. Such trypsin-like endopeptidase may have optimal proteolytic activity at a pH from about 5.0 to about 11.0, preferably at a pH from about 8 to about 11, and at a temperature from about 40° C. to about 75° C., preferably at a temperature from about 40° C. to about 60° C. It may be inhibited by EDTA.

The trypsin-like endopeptidase may be produced by the strain from which it is derived. Or it may be produced from a recombinant host cell comprising a polynucleotide encoding the endopeptidase operably linked to one or more (several) control sequences that direct its production. A construct or vector comprising a polynucleotide is introduced into a host cell so that the construct or vector is maintained as a chromosomal integrant or as a self-replicating extra-chromosomal vector.

The host cell may be any cell useful in the recombinant production of the endopeptidase, e.g., a prokaryote or a eukaryote.

The prokaryotic host cell may be any gram-positive or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The host cell may also be a eukaryote, such as a mammalian, insect, plant, or fungal cell.

The trypsin-like endopeptidase is preferably an isolated trypsin-like endopeptidase. The concentration of trypsin-like endopeptidase may be 100-500,000 USP Trypsin Units per g food protein, e.g., 250-250,000 or 500-100,000.

One USP Trypsin Unit is the activity causing a change in absorbance at 253 nm of 0.003 at pH 7.6 and 25° C. using N-benzoyl-L-arginine ethyl ester hydrochloride (BAEE) as substrate.

The specific activity may vary quite significantly among different trypsin-like endopeptidases, but the skilled person will easily be able to determine in which amount the trypsin-like endopeptidase is to be used, e.g. based on the degree of hydrolysis.

The ratio of trypsin-like endopeptidase to food protein is preferably 0.01-5% weight/weight, more preferably 0.01-2%, more preferably 0.05-0.8%, even more preferably 0.1-0.6%, and most preferably around 0.2%.

Optional Inclusion of Another Endopeptidase being Less Specific

In a preferred embodiment, at least one other endopeptidase is added to the solution before, during or after step (b).

Preferably, the at least one other endopeptidase is an isolated endopeptidase.

Preferably, the at least one other endopeptidase is a serine endopeptidase.

In a preferred embodiment, the at least one other endopeptidase has an activity which is less specific than the trypsin-like endopeptidase.

In another preferred embodiment, the at least one other endopeptidase has an activity which resembles the activity of mammalian chymotrypsin, e.g., chymotrypsin extracted from porcine pancreatic tissue.

In another preferred embodiment, the at least one other endopeptidase has a higher specificity for cleaving at the carboxy-terminal side of either of tyrosine, phenylalanine, tryptophan, leucine, methionine or histidine than for cleaving on the carboxy-terminal side of any other natural amino acid.

In another preferred embodiment, the at least one other endopeptidase has a specificity for cleaving at the carboxy-terminal side of at least one of tyrosine, phenylalanine, tryptophan, leucine, methionine or histidine, which is at least 3-fold higher, preferably at least 5-fold higher, than its specificity for cleaving at the carboxy-terminal side of either one of alanine, arginine, asparagine, aspartic acid, cysteine, glutamic acid, glutamine, glycine, isoleucine, lysine, proline, serine, threonine and valine.

In another preferred embodiment, the at least one other endopeptidase has a higher specificity for cleaving at the carboxy-terminal side of each of at least three amino acids from the group consisting of tyrosine, phenylalanine, tryptophan, leucine, methionine and histidine than for cleaving on the carboxy-terminal side of arginine.

In another preferred embodiment, the at least one other endopeptidase has a higher specificity for cleaving at the carboxy-terminal side of each of at least three amino acids from the group consisting of tyrosine, phenylalanine, tryptophan, leucine, methionine and histidine than for cleaving on the carboxy-terminal side of lysine.

In another preferred embodiment, the at least one other endopeptidase has a higher specificity for cleaving at the carboxy-terminal side of each of tyrosine, phenylalanine, tryptophan, leucine, methionine and histidine than for cleaving on the carboxy-terminal side of both of arginine and lysine.

In another preferred embodiment, the at least one other endopeptidase has a Chymotrypsin ratio of at least 3, preferably at least 5. A Chymotrypsin ratio of at least 5 means that the activity of the enzyme when cleaving after one of Phe, Leu or Met (whichever is the larger) is at least five times higher than the activity when cleaving after any one of Ala, Arg, Asp, Glu, Ile, Lys or Val (whichever is the larger). I.e., the at least one other endopeptidase has a specificity for cleaving after one of Phe, Leu or Met (whichever is the larger) which is at least 3-fold higher, preferably at least 5-fold higher, than its specificity for cleaving after any one of Ala, Arg, Asp, Glu, Ile, Lys or Val (whichever is the larger). Such activity measurements to determine the Chymotrypsin ratio should be performed at a pH-value where the activity of the endopeptidase is at least half of the activity of the endopeptidase at its pH optimum. The Chymotrypsin ratio may be determined as described in Example 1 of patent application no. WO 2010/112546.

In another preferred embodiment, the at least one other endopeptidase is a bacterial endopeptidase.

In a more preferred embodiment, the at least one other endopeptidase is derived from a strain of *Nocardiopsis*, preferably from *Nocardiopsis* sp. NRRL 18262 (previously described in, e.g., WO 88/03947). It may, e.g., have the amino acid sequence of the mature polypeptide of SEQ ID NO: 7 of the present application. The DNA and amino acid sequences of the protease derived from *Nocardiopsis* sp. NRRL 18262 have previously been published in, e.g., DK patent application no. 1996 00013.

In another more preferred embodiment, the at least one other endopeptidase is derived from *Metarhizium*, preferably *Metarhizium anisopliae*, e.g. having the amino acid sequence of the mature polypeptide of SEQ ID NO: 8 of the present application (TREMBL:Q9Y843). In another more preferred embodiment, the at least one other endopeptidase is derived from *Brachysporiella*, preferably *Brachysporiella gayana*, e.g. having the amino acid sequence of the mature polypeptide of SEQ ID NO: 9 of the present application (CGMCC 0865). The DNA and amino acid sequences of the proteases derived from *Metarhizium anisopliae* and *Brachysporiella gayana* have previously been published in, e.g., WO04072279.

In another preferred embodiment, the at least one other endopeptidase has a sequence identity to the mature polypeptide of any of SEQ ID NOs: 7, 8 or 9 of at least 70%, at least 75%, at least 80%, at least 85%, at least 90%, at least 95%, at least 96%, at least 97%, at least 98%, at least 99%, or 100%. In another preferred embodiment, the at least one other endopeptidase differs by no more than ten amino acids, e.g., by five amino acids, by four amino acids, by three amino acids, by two amino acids, or by one amino acid from the mature polypeptide of any of SEQ ID NOs: 7, 8 or 9.

The mature polypeptide of SEQ ID NO: 7 may be amino acids 1-188. The mature polypeptide of SEQ ID NO: 8 may be amino acids 187-374. The mature polypeptide of SEQ ID NO: 9 may be amino acids 190-375.

In a more preferred embodiment, the at least one other endopeptidase has a sequence identity to the mature polypeptide of SEQ ID NO: 7 of at least 70%, at least 75%, at least 80%, at least 85%, at least 90%, at least 95%, at least 96%, at least 97%, at least 98%, at least 99%, or 100%. In another preferred embodiment, the at least one other endopeptidase differs by no more than ten amino acids, e.g., by five amino acids, by four amino acids, by three amino acids, by two amino acids, or by one amino acid from the mature polypeptide of SEQ ID NO: 7.

The concentration of the at least one other endopeptidase is preferably 100-100,000 USP Chymotrypsin Units per g food protein, more preferably 500-50,000, and most preferably 1,000-20,000.

One USP Chymotrypsin Unit is the activity causing a change in absorbance at 237 nm of 0.0075 at pH 7.0 and 25° C. using N-acetyl-L-tyrosine ethyl ester (ATEE) as substrate.

The specific activity may vary quite significantly among different endopeptidases, but the skilled person will easily be able to determine in which amount the at least one other endopeptidase is to be used, e.g. based on the degree of hydrolysis.

The ratio of the at least one other endopeptidase to food protein is preferably 0.001-1% weight/weight, more preferably 0.001-0.5%, more preferably 0.005-0.25%, and most preferably 0.01-0.05%.

Preferably, the at least one other endopeptidase is added at a concentration which is between 1% and 50% of the concentration of trypsin-like endopeptidase added based on the weight of the endopeptidases. In one preferred embodiment, the at least one other endopeptidase is added at a concentration which is between 2% and 20% w/w of the trypsin-like endopeptidase, preferably between 3% and 5%. In another preferred embodiment, the at least one other endopeptidase is added at a concentration which is between 5% and 15% w/w of the trypsin-like endopeptidase, preferably about 10%.

Food Protein Hydrolysate

An optional preliminary step prior to hydrolysis is preheating of the solution comprising food protein. In a preferred embodiment, a pre-treatment step is performed which comprises heating of the food protein at about 75-95° C. for about 5-30 minutes. In another preferred embodiment, a pre-treatment step is performed which comprises heating of the food protein at above 135° C. for about 1-5 seconds. In another preferred embodiment, a pre-treatment step is performed which comprises heating of the food protein at about 130° C. for about 30-60 seconds.

The skilled person will know which conditions to preferably apply for the hydrolysis reaction. It may, e.g., be conducted at a temperature of about 40° C. to 60° C., during 1 to 6 hours, at pH values within the range 6.5 to 8.5, preferably 6.5 to 8.

In a preferred embodiment, following a first treatment with the endopeptidase, the proteinaceous material is further subjected to a second proteolytic hydrolysis followed by endopeptidase inactivation. In a more preferred embodiment, the proteinaceous material is subjected to a heat treatment in between the first and the second proteolytic hydrolysis as disclosed in U.S. Pat. No. 5,039,532, which is hereby incorporated by reference.

Irrespective of the conditions of the hydrolysis, the hydrolysate preferably is subjected to an additional step of inactivation of the endopeptidase. This peptidase inactivation in a preferred embodiment comprises a heat treatment of about 0.1 to 30 min at a temperature of about 70 to 110° C., preferably 75 to 95° C. Alternatively, the endopeptidase may be inactivated by sterilization at ultra-high temperature (e.g., at about 130° C. for about 30-60 seconds).

The food protein hydrolysate obtained may be further treated. It may be clarified. It may be stored in a liquid state.

The hydrolysate may also be ultrafiltrated, it may be concentrated, e.g., by evaporation, and it may be dried, e.g., by spray drying or lyophilization.

In a preferred embodiment, the food protein hydrolysate obtained has a moderate degree of hydrolysis. In another preferred embodiment, the food protein hydrolysate obtained is a partial hydrolysate. In another preferred embodiment, the food protein hydrolysate obtained has a degree of hydrolysis of between 5 and 30%, preferably between 6 and 15%. A particularly preferred degree of hydrolysis is around 14%. Another particularly preferred degree of hydrolysis is around 15%.

The degree of hydrolysis (DH) expresses the extent of the protein hydrolysis obtained by the method. In the context of the invention, the degree of hydrolysis (DH) is defined as follows:

DH=(Number of peptide bonds cleaved/Total number of peptide bonds)×100%

Degree of hydrolysis (DH) of the protein hydrolysate obtained may be measured spectrophotometrically according to the method of Church, F. C. et al. (1983) Spectrophotometric Assay Using o-Phthaldialdehyde for Determination of Proteolysis in Milk and Isolated Milk Proteins, *J. Dairy Sci.* 66: 1219-1227.

The molecular weight distribution of the peptides in the food protein hydrolysate obtained may be determined, e.g., by size exclusion chromatography (SEC). In a preferred embodiment, the hydrolysate of the invention is comprised of peptides where less than 1% on a weight-basis has a molecular weight of above 20,000 kDa.

The food protein hydrolysate obtained by the method of the invention is preferably devoid of detectable intact food protein. The absence of intact food protein in the hydrolysate may be demonstrated by sodium dodecylsulfate-polyacrylamide gel electrophoresis (SDS-PAGE). Direct comparison between a hydrolysate and the non-hydrolyzed protein starting material can be made in the same gel. In a preferred embodiment, the hydrolysate of the invention is comprised of peptides where less than 1% on a weight-basis is intact food protein.

The residual antigenicity of the hydrolysate obtained by the method of the invention may be determined using an enzyme-linked immunosorbent assay (ELISA). Non-hydrolyzed food protein is immobilized on a solid phase at concentrations that fall within the linear dose response range established in the assay. Hydrolysate preparations are similarly immobilized. Subsequent, sequential incubations with rabbit antibody and an enzyme conjugate reactive with rabbit IgG reveals the presence of antigenically recognizable proteins and peptides. Results obtained with the hydrolysate are compared on a mass basis to those obtained with the non-hydrolyzed protein starting material. The percent antigenicity reduction of the hydrolysate is then calculated.

In a preferred embodiment, the food protein hydrolysate obtained by a method of the invention has a reduction in antigenicity of at least about 80%, preferably at least about 85%, more preferably at least about 90% or at least about 95%, most preferably at least about 98%, and even most preferably the reduction in antigenicity is at least about 99%, relative to the corresponding non-hydrolyzed food protein material as measured by ELISA.

The present invention is further described by the following examples that should not be construed as limiting the scope of the invention.

EXAMPLES

Example 1

Cloning and Expression of a Trypsin-Like Endopeptidase from *Kutzneria albida*

Gene:

The *Kutzneria albida* trypsin-like endopeptidase was expressed from a synthetic gene in *Bacillus subtilis*. The synthetic gene sequence was designed based on SEQ ID NO: 2 (*Kutzneria albida* mature trypsin-like endopeptidase) and codon optimized for expression in *Bacillus subtilis*. The expressed DNA sequence was SEQ ID NO: 3. The *Kutzneria albida* trypsin-like endopeptidase was expressed with a Savinase® secretion signal (with the following amino acid sequence: MKKPLGKIVASTALLISVAFSSSIASA (SEQ ID NO: 4)) replacing the native secretion signal. Nucleotides 1-81 of SEQ ID NO: 3 is the DNA sequence of the Savinase secretion signal and nucleotides 82-756 encode the mature polypeptide.

Expression Vector:

ExpVec8 was used as expression vector and a plasmid map is shown in FIG. 1. The vector makes it possible to integrate the gene construct on the *Bacillus subtilis* chromosome by homologous recombination into the pectate lyase locus of the *Bacillus subtilis* host. The gene was expressed from the triple promoter system consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. (as described in WO 99/43835). The ExpVec8 contains a savinase signal peptide, a savinase terminator, a chloramphenicol resistance gene to make selection for integrants in *Bacillus subtilis* possible, an amplicillin resistance gene (bla), a kanamycin resistance gene (neo), and an *E. coli* origin of replication.

Expression Cloning:

The standard cloning vector containing the synthetic gene was transformed into *E. coli* (dam−/dcm− from New England BioLabs deficient in the methylation of adenine and cytosine residues in DNA). The plasmid was purified and digested with ClaI and MluI to release the insert with the synthetic gene. ExpVec8 was used as expression vector and was digested with the same restriction enzymes (ClaI and MluI). Vector and the purified fragment were ligated and transformed into *E. coli* (Top10, Invitrogen). The expression plasmid containing the insert was purified from one of the transformants and re-transformed into *Bacillus subtilis*. A recombinant *Bacillus subtilis* clone containing the integrated expression construct were grown in liquid culture. The enzyme containing supernatant was harvested and the enzyme purified as described in Example 2.

Example 2

Purification and Characterization of the AC3 Trypsin-Like Endopeptidase from Kutzneria Albida Purification Activity Assay:

pNA substrate: Boc-VLGR[SEQ ID NO: 10]-pNA (Bachem L-1205).

Temperature: Room temperature (25° C.)

Assay buffer: 100 mM succinic acid, 100 mM HEPES, 100 mM CHES, 100 mM CABS, 1 mM $CaCl_2$, 150 mM KCl, 0.01% Triton X-100, pH 6.0.

20 µl protease (diluted in 0.01% Triton X-100) is dispensed in a microtiter plate well. The assay is started by adding 200 µl pNA substrate (50 mg Boc-VLGR[SEQ ID NO: 10]-pNA dissolved in 1.0 ml DMSO and further diluted 90× with Assay buffer). The initial increase in OD$_{405}$ is monitored as a measure of the protease activity.

Characterization Activity Assays:

1) pNA Assay:

pNA substrates: Boc-VLGR[SEQ ID NO: 10]-pNA (Bachem L-1205)
  Suc-AAPF[SEQ ID NO: 11]-pNA (Bachem L-1400)
  Suc-AAPA[SEQ ID NO: 12]-pNA (Bachem L-1775)
  Suc-AAPR[SEQ ID NO: 13]-pNA (Bachem L-1720)
  Suc-AAPD[SEQ ID NO: 14]-pNA (Bachem L-1835)
  Suc-AAPE[SEQ ID NO: 15]-pNA (Bachem L-1710)
  Suc-AAPI[SEQ ID NO: 16]-pNA (Bachem L-1790)
  Suc-AAPL[SEQ ID NO: 17]-pNA (Bachem L-1390)
  Suc-AAPK[SEQ ID NO: 18]-pNA (Bachem L-1725)
  Suc-AAPM[SEQ ID NO: 19]-pNA (Bachem L-1395)
  Suc-AAPV[SEQ ID NO: 20]-pNA (Bachem L-1770)

Temperature: Room temperature (25° C.)

Assay buffers: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 2.5, 3.0, 3.5, 4.0, 5.0, 6.0, 7.0, 8.0, 9.0, 10.0, 11.0, and 12.0 with HCl or NaOH.

20 µl protease (diluted in 0.01% Triton X-100) is mixed with 100 µl assay buffer. The assay is started by adding 100 µl pNA substrate (50 mg dissolved in 1.0 ml DMSO and further diluted 45× with 0.01% Triton X-100). The initial increase in OD$_{405}$ is monitored as a measure of the protease activity.

2) Protazyme AK Assay:

Substrate: Protazyme AK tablet (cross-linked and dyed casein; from Megazyme)

Temperature: Controlled (assay temperature).

Assay buffers: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.

A Protazyme AK tablet is suspended in 2.0 ml 0.01% Triton X-100 by gentle stirring. 500 µl of this suspension and 500 µl assay buffer are mixed in an Eppendorf tube and placed on ice. 20 µl protease sample (diluted in 0.01% Triton X-100) is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200 µl supernatant is transferred to a microtiter plate. OD$_{650}$ is read as a measure of protease activity. A buffer blank is included in the assay (instead of enzyme).

Purification of the AC3 Trypsin-Like Protease from *Kutzneria albida*

The culture broth from Example 1 was centrifuged (20000×g, 20 min) and the supernatants were carefully decanted from the precipitates. The combined supernatants were filtered through a Nalgene 0.2 µm filtration unit in order to remove the rest of the *Bacillus* host cells. The 0.2 µ filtrate was precipitated with ammonium sulphate by addition of solid ammonium sulphate to 3.4M final (NH$_4$)$_2$SO$_4$ concentration. The formed precipitate was collected by centrifugation (20000×g, 20 min) and the precipitate was dissolved in a minimal volume of deionized water. The solution was transferred to 50 mM H$_3$BO$_3$, 5 mM MES, 1 mM CaCl$_2$, pH 6 on a G25 Sephadex® column and applied to an S-sepharose® HP column equilibrated in the same buffer. After washing the column extensively with the equilibration buffer, the protease was eluted with a linear NaCl gradient (0-->0.5M) in the same buffer. Fractions from the column were analysed for protease activity (Purification activity assay). Solid ammonium sulphate was added to the BOC-VLGR[SEQ ID NO: 10]-pNA activity peak from the S-sepharose HP column to give a 1.6 M final (NH$_4$)$_2$SO$_4$ concentration in the enzyme solution. The enzyme solution was mixed gently with a magnetic stirrer during the (NH$_4$)$_2$SO$_4$ addition and the stirring was continued for 30 minutes after the addition to bring the system in equilibrium. Then the enzyme solution was applied to a Phenyl-sepharose FF (high sub) column equilibrated in 100 mM H$_3$BO$_3$, 10 mM MES, 2mM CaCl$_2$, 1.6M (NH$_4$)$_2$SO$_4$, pH 6. After washing the column extensively with the equilibration buffer, the AC3 trypsin protease was eluted with a linear (NH$_4$)$_2$SO$_4$ gradient (1.6-->0M) in the same buffer. Fractions from the column were analysed for protease activity (Purification activity assay) and active fractions were further analysed by SDS-PAGE. Fractions, where only one band was seen on the coomassie stained SDS-PAGE gel, were pooled and transferred to 100 mM H$_3$BO$_3$, 10 mM MES, 2 mM CaCl$_2$, pH 6 on a G25 sephadex column as the purified preparation and was used for further characterization.

Characterization: ph-Activity, pH-Stability, and Temperature-Activity

The pNA assay was used for obtaining the pH-activity profile on Boc-VLGR[SEQ ID NO: 10]-pNA and on Suc-AAPR[SEQ ID NO: 13]-pNA as well as for the pH-stability profile. For the pH-stability profile the protease was diluted 10× in the assay buffers and incubated for 2 hours at 37° C. After incubation the protease samples were transferred to pH 9, before assay for residual activity, by dilution in the pH 9 Assay buffer. The Protazyme AK assay was used for obtaining the pH-activity profile at 37° C. and the temperature-activity profile at pH 7. The results are shown in Tables 1-3 below. For Table 1, the activities are relative to the optimal pH for the enzyme for each substrate. For Table 2, the activities are residual activities relative to a sample, which was kept at stable conditions (5° C., pH 9). For Table 3, the activities are relative to the optimal temperature at pH 7 for the enzyme.

TABLE 1 pH-activity profiles

| pH | AC3 trypsin on Boc-VLGR [SEQ ID NO: 10]-pNA | AC3 trypsin on Suc-AAPR [SEQ ID NO: 13]-pNA | AC3 trypsin on Protazyme AK |
|---|---|---|---|
| 2 | 0.00 | 0.00 | 0.00 |
| 3 | 0.01 | 0.01 | 0.00 |
| 4 | 0.06 | 0.04 | 0.00 |
| 5 | 0.30 | 0.14 | 0.01 |
| 6 | 0.79 | 0.41 | 0.67 |
| 7 | 1.00 | 0.66 | 1.00 |
| 8 | 0.87 | 0.96 | 0.71 |
| 9 | 0.77 | 1.00 | 0.50 |
| 10 | 0.61 | 0.97 | 0.28 |
| 11 | 0.48 | 0.86 | 0.16 |
| 12 | 0.00 | — | — |

TABLE 2 pH-stability profile

| pH | AC3 trypsin |
| --- | --- |
| 2.0 | 0.00 |
| 2.5 | 0.00 |
| 3.0 | 0.78 |
| 3.5 | 1.01 |
| 4.0 | 1.01 |
| 5.0 | 1.00 |
| 6.0 | 1.00 |
| 7.0 | 0.99 |
| 8.0 | 0.98 |
| 9.0 | 0.99 |
| 10.0 | 1.03 |
| 11.0 | 0.61 |
| 12.0 | 0.01 |
| 9.0 and after 2 hours at 5° C. | 1.00 |

TABLE 3

Temperature activity profile at pH 7.0

| Temp (° C.) | AC3 trypsin on Protazyme AK |
| --- | --- |
| 15 | 0.05 |
| 25 | 0.07 |
| 37 | 0.20 |
| 50 | 0.45 |
| 60 | 1.00 |
| 70 | 0.74 |
| 80 | 0.19 |

Characterization: P1-specificity on Suc-AAPX[SEQ ID NO: 21]-pNA substrates and calculation of the Trypsin ratio The pNA assay was used for obtaining the P1-specificity for the AC3 trypsin protease using 10 Suc-AAPX[SEQ ID NO: 21]-pNA substrates at two different pH-values: pH 7.0 and pH 9.0. The activities were also used to calculate the trypsin ratio as defined in WO 2010/112546. The results are shown in Table 4 below. For Table 4, the activity for each Suc-AAPX[SEQ ID NO: 21]-pNA substrate is relative to the activity for the best Suc-AAPX[SEQ ID NO: 21]-pNA substrate (Suc-AAPR[SEQ ID NO: 13]-pNA).

TABLE 4

P1-specificity on Suc-AAPX[SEQ ID NO: 21]-pNA and Trypsin ratio

| Suc-AAPX [SEQ ID NO: 21]-pNA | AC3 trypsin pH 7 | AC3 trypsin pH 9 |
| --- | --- | --- |
| Suc-AAPA [SEQ ID NO: 12]-pNA | 0.00001 | 0.00000 |
| Suc-AAPR [SEQ ID NO: 13]-pNA | 1.00000 | 1.00000 |
| Suc-AAPD [SEQ ID NO: 14]-pNA | 0.00000 | 0.00000 |
| Suc-AAPI [SEQ ID NO: 16]-pNA | 0.00000 | 0.00000 |
| Suc-AAPM [SEQ ID NO: 19]-pNA | 0.00002 (0.0000151) | 0.00001 (0.0000113) |
| Suc-AAPV [SEQ ID NO: 20]-pNA | 0.00000 | 0.00000 |
| Suc-AAPL [SEQ ID NO: 17]-pNA | 0.00001 | 0.00000 |
| Suc-AAPE [SEQ ID NO: 15]-pNA | 0.00001 | 0.00000 |
| Suc-AAPK [SEQ ID NO: 18]-pNA | 0.67242 | 0.49569 |
| Suc-AAPF [SEQ ID NO: 11]-pNA | 0.00001 | 0.00001 (0.0000086) |
| Max of Suc-AAP(R/K) [SEQ ID NO: 22]-pNA | 1.00000 | 1.00000 |
| Max of Suc-AAPnon(R/K) [SEQ ID NO: 23]-pNA | 0.00002 (0.0000151) | 0.00001 (0.0000113) |
| Trypsin ratio | 66000 | 88000 |

Other Characteristics

The AC3 trypsin protease is inhibited by aprotinin.

The relative molecular weight as determined by SDS-PAGE was $M_r=26$ kDa.

The N-terminal sequence was determined as: IVGGT-KASTSTY [SEQ ID NO: 24].

The Intact molecular weight was determined to be Mw=23087.67 Da.

These data indicate that the mature AC3 trypsin protease has the following sequence (amino acids 1 to 225 of SEQ ID NO: 2):

IVGGTKASTSTYPFVVFLTDSTGFQFCGGTLVKPNKVVTAAHCTVGESAA

NIRVVAGRDDKQSTAGTVSKVSKIWIHPSYQDATKGSDVSVLTLSTSLTQ

FTPLPLAATTDTALYKEGTAATILGWGDTTEGGSASRYLLKATVPLTSDA

TCKKAYGEYSSTAMVCAGYPQGGTDTCQGDSGGPLVAGNKLIGITSWGQG

CAEAGYPGVYTRVATYSSLITQQLG

Example 3

Cleavage Specificity Analysis of the AC3 Trypsin-Like Endopeptidase from *Kutzneria Albida*

Introduction:

The proteolytic cleavage specificity of the microbial trypsin-like endopeptidase, AC3, was compared with porcine trypsin.

The cleavage specificity analyses was performed by incubation of the described endopeptidases with the native model substrate bovine BioPURE-Alphalactalbumin from Davisco Foods international. The peptide profiles of the resulting proteolytic peptides were determined by RP-HPLC separation and UV signal detection at 214 nm.

Samples:

Proteases: Porcine trypsin (UniProt accession: P00761)

AC3 (trypsin-like endopeptidase from *Kutzneria albida*)

Substrate: Alpha Lactalbumin from Davisco, BE-2009-00036, 97% protein from Davisco Foods international Proteolysis:

1 g of Alphalactalbumin was dissolved in 17.6 ml of 5 mM $CaCl_2$. The sample was heated to 55° C. and pH was adjusted to 7.5 with 0.25 M NaOH. Enzyme was added at a ratio of 2 mg enzyme per gram alphalactabumin. pH titration was carried out on Titralab 856 for 120 min. 200 µl samples were taken out after 120 min and stopped by adding 2.2 µl trifluoroacetic acid (TFA). The sample was stored at −20° C. prior to RP-HPLC analysis.

RP-HPLC Analysis:

The proteolytic samples were analyzed on a RP-HPLC system consisting of Waters C18 column (ACQUITY UPLC® BEH C18, 1.7 μm, 2.1×100 mm) and an Accela liquid chromatography system from Thermo Scientific. All samples were diluted 5× in 0.1% TFA (10 μl sample+40 μl 0.1% TFA). A volume of 5 μl was injected onto the column. The peptides were separated by the following gradient:

All samples were diluted 5×. Injection volume: 5 μl.

Solvent A: 0.1% TFA (CAS number 76-05-1) in UHQ water and solvent B: 0.08% TFA in acetonitrile (CAS number 75-05-8)

| Time (min) | % B solvent |
|---|---|
| 0 | 5 |
| 2 | 5 |
| 49 | 50 |
| 51 | 90 |
| 53 | 90 |
| 55 | 5 |
| 60 | 5 |

The eluting peptides were monitored online by a UV-detector at 214 nm.

Figure 2:
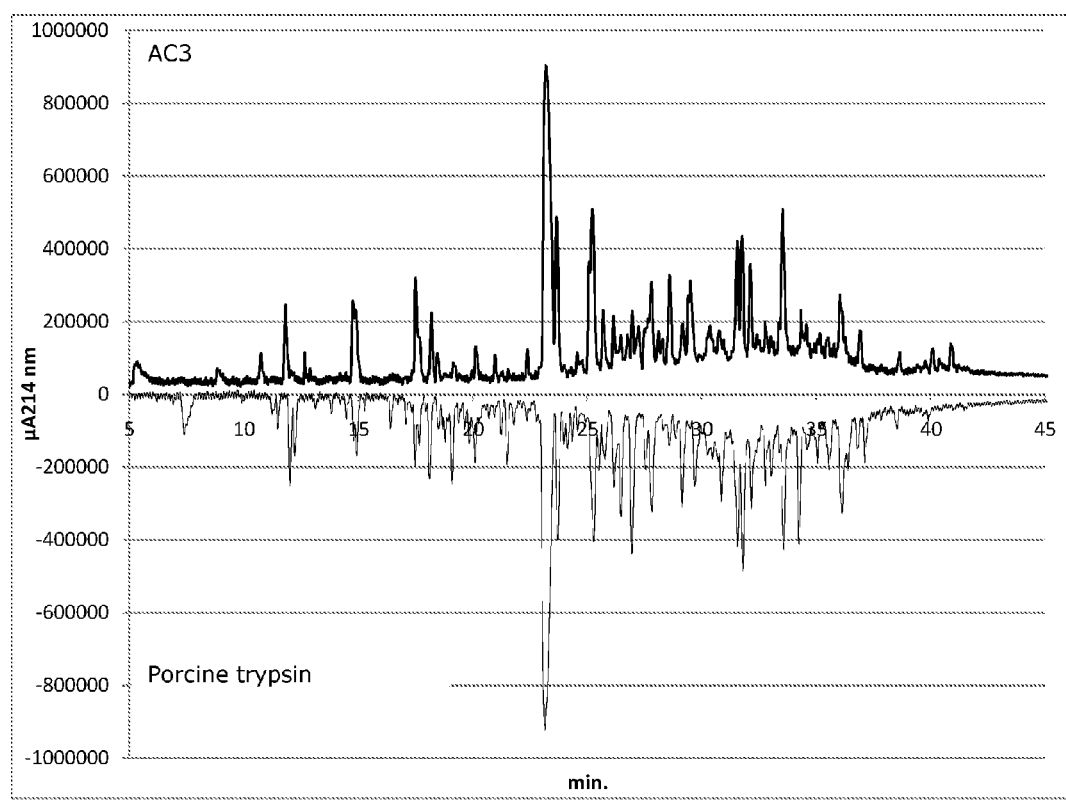
FIG. 2 shows UV chromatograms of bovine alphalactalbumin hydrolysed with the trypsin-like endopeptidase from *Kutzneria albida* (upper trace) or porcine trypsin (bottom trace).

Results:

For comparison, the UV-chromatogram of the AC3 assay (upper trace) is displayed in FIG. 2 together with porcine trypsin assay (bottum trace).

Conclusion:

The RP-HPLC peptide profile of alphalactalbumin hydrolysed by AC3 is similar to the peptide profile produced by porcine trypsin; thus AC3 has trypsin like specificity.

Example 4

Hydrolysis of Whey Protein Concentrate and of Alpha Lactalbumin with AC3 Trypsin-Like Protease in Comparison with Porcine Derived Trypsin Materials:

Whey protein concentrate (WPC), 80% dry matter protein, Lacprodan 80, Arla Foods Ingredients, DK Alpha lactalbumin (ALA), 97% dry matter protein, Davisco Foods International, MN, US CaCl$_2$ anhydrous, Merck art 2387

NaOH, Prolabo 31627.368

Hydrolysis Assay:

1 g Alpha-lactalbumin dissolved in 17.6 ml of 5 mM CaCl$_2$ or 1.2 g Lacprodan 80 in 17.4 ml of 5 mM CaCl$_2$ were produced to obtain a final protein concentration of 5%.

Samples were heated to 55° C. and pH was adjusted to 7.5. The NaOH volume consumed for pH adjustment was recorded. Enzyme was added and pH titration was carried out on Titralab 856 (Radiometer) for 120 min. NaOH consumption was monitored and converted into % DH.

Degree of Hydrolysis:

Degree of hydrolysis of the suspension was measured by pH stat as described in Adler-Nissen, J. 1986, Enzymatic Hydrolysis of Food Proteins, Chapter 6.

Degree of Hydrolysis (DH) defined as the percentage of peptide bonds cleaved can be monitored with pH-stat technique: $DH = h/h_{tot} \times 100$ h: number of peptide bonds cleaved, proportional to the amount of base consumed during the reaction.

$h_{tot}$: number of peptide bonds in a protein calculated from the amino acid composition.

$h_{tot}$ for ALA=8.16 and $h_{tot}$ for WPC=8.8

$h = B \times Nb \times 1/\alpha \times 1/Mp$

B=base consumption (ml)

Nb=Normality of the base (0.25 N)

$1/\alpha$ =average degree of dissociation of the α-NH$_2$ groups

Mp=Protein mass (g), (N×Kjeldahl factor)

Endopeptidases Used:

| Enzyme | Trypsin Conc. (mg/ml) |
|---|---|
| AC3 trypsin-like protease from *Kutzneria albida* | 1.3 mg/ml |
| Trypsin, chromatographically purified from Porcine trypsin (PTN 6.0S) | 9.5 mg/ml |

Data:

ALA:

| | Dosage | DH (120 min) |
|---|---|---|
| AC3 trypsin-like protease from *Kutzneria albida* | 2 mg enzyme protein/g protein | 6.9 |
| Trypsin, chromatographically purified from Porcine trypsin (PTN 6.0S) | 2 mg enzyme protein/g protein | 9.0 |

WPC:

| | Dosage | DH (120 min) |
|---|---|---|
| AC3 trypsin-like protease from *Kutzneria albida* | 2 mg enzyme protein/g protein | 6.0 |
| Trypsin, chromatographically purified from Porcine trypsin (PTN 6.0S) | 2 mg enzyme protein/g protein | 7.6 |

Conclusion:

Both in the whey protein fraction alpha lactalbumin and in the whey protein concentrate, it seems to be possible to get a degree of hydrolysis (DH) in the same range by using the microbial derived AC3 trypsin-like protease as when using porcine trypsin chromatographically purified from PTN 6.0S.

Example 5

Purification and Characterization of Trypsin-Like Endopeptidase from *Actinosynnema Mirum*

Purification Activity Assay:

pNA substrate: Suc-AAPR[SEQ ID NO: 13]-pNA (Bachem L-1720).

Temperature: Room temperature (25° C.)

Assay buffer: 100 mM succinic acid, 100 mM HEPES, 100 mM CHES, 100 mM CABS, 1 mM CaCl$_2$, 150 mM KCl, 0.01% Triton X-100, pH 9.0.

20 μl protease (diluted in 0.01% Triton X-100) is dispensed in a microtiter plate well. The assay is started by adding 200 μl pNA substrate (50 mg Suc-AAPR[SEQ ID NO: 13]-pNA dissolved in 1.0 ml DMSO and further diluted 90× with Assay buffer). The initial increase in OD$_{405}$ is monitored as a measure of the protease activity.

Characterization Activity Assays:

1) pNA Assay:

pNA substrates: Suc-AAPR[SEQ ID NO: 13]-pNA (Bachem L-1720)
Suc-AAPF[SEQ ID NO: 11]-pNA (Bachem L-1400)
Suc-AAPA[SEQ ID NO: 12]-pNA (Bachem L-1775)
Suc-AAPD[SEQ ID NO: 14]-pNA (Bachem L-1835)
Suc-AAPE[SEQ ID NO: 15]-pNA (Bachem L-1710)
Suc-AAPI[SEQ ID NO: 16]-pNA (Bachem L-1790)
Suc-AAPL[SEQ ID NO: 17]-pNA (Bachem L-1390)
Suc-AAPK[SEQ ID NO: 18]-pNA (Bachem L-1725)
Suc-AAPM[SEQ ID NO: 19]-pNA (Bachem L-1395)
Suc-AAPV[SEQ ID NO: 20]-pNA (Bachem L-1770)

Temperature: Room temperature (25° C.)

Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease (diluted in 0.01% Triton X-100) is mixed with 100 µl assay buffer. The assay is started by adding 100 µl pNA substrate (50 mg dissolved in 1.0 ml DMSO and further diluted 45× with 0.01% Triton X-100). The initial increase in $OD_{405}$ is monitored as a measure of the protease activity.

2) Protazyme AK Assay:

Substrate: Protazyme AK tablet (cross-linked and dyed casein; from Megazyme)

Temperature: Controlled (assay temperature).

Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.

A Protazyme AK tablet is suspended in 2.0 ml 0.01% Triton X-100 by gentle stirring. 500 µl of this suspension and 500 µl assay buffer are mixed in an Eppendorf tube and placed on ice. 20 µl protease sample (diluted in 0.01% Triton X-100) is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200 µl supernatant is transferred to a microtiter plate. $OD_{650}$ is read as a measure of protease activity. A buffer blank is included in the assay (instead of enzyme).

Purification of the Trypsin-Like Protease from Strain RBPO0013

RBPO00013 is a *Bacillus subtilis* strain constructed to express to the culture medium the mature trypsin-like protease from *Actinosynnema mirum*, the amino acid sequence of which is shown as SEQ ID NO: 5 of the present application.

The RBPO0013 culture broth was centrifuged (20000×g, 20 min) and the supernatants were carefully decanted from the precipitates. The combined supernatants were filtered through a Nalgene 0.2 µm filtration unit in order to remove the rest of the *Bacillus* host cells. Solid ammonium sulphate was added to the 0.2 µm filtrate to 1.8M final $(NH_4)_2SO_4$ concentration. The filtrate was mixed gently with a magnetic stirrer during the $(NH_4)_2SO_4$ addition and the stirring was continued for 30 minutes after the addition to bring the system in equilibrium. Then the solution was applied to a Phenyl Toyopearl 650S column (TosoHaas) equilibrated in 100 mM $H_3BO_3$, 10 mM MES, 2 mM $CaCl_2$, 1.8M $(NH_4)_2SO_4$, pH 6. After washing the column extensively with the equilibration buffer, the trypsin-like protease was eluted with a linear $(NH_4)_2SO_4$ gradient (1.6-->0M) in the same buffer. Fractions from the column were analysed for trypsin-like protease activity (Purification activity assay) and fractions forming the major activity peak were pooled. The pool from the Phenyl Toyopearl column was transferred to 50 mM $H_3BO_3$, 5 mM MES, 1 mM $CaCl_2$, pH 6 on a G25 sephadex column (GE Healthcare) and applied to an S-sepharose FF column (GE Healthcare) equilibrated in the same buffer. After washing the column extensively with the equilibration buffer, the protease was eluted with a linear NaCl gradient (0-->0.5M) in the same buffer. Fractions from the column were analysed for trypsin-like protease activity (Purification activity assay) and active fractions were further analysed by SDS-PAGE. Fractions, which were seen to be at least 90% pure on a coomassie stained SDS-PAGE gel, were pooled and was used for further characterization.

Characterization: ph-Activity, pH-stability, and Temperature-activity

The pNA assay was used for the pH-activity profile on Suc-AAPR[SEQ ID NO: 13]-pNA and for the pH-stability profile. For the pH-stability profile the protease was diluted 10× in the assay buffers and incubated for 2 hours at 37° C. After incubation the protease samples were transferred to pH 9, before assay for residual activity, by dilution in the pH 9 Assay buffer. The Protazyme AK assay was used for obtaining the temperature-activity profile at pH 7. The results are shown in Tables 5-7 below. For Table 5, the activities are relative to the optimal pH for the enzyme. For Table 6, the activities are residual activities relative to a sample, which was kept at stable conditions (5° C., pH 9). For Table 7, the activities are relative to the optimal temperature at pH 7 for the enzyme.

TABLE 5 pH-activity profile

| pH | *Actinosynnema mirum* trypsin |
|---|---|
| 2 | 0.00 |
| 3 | 0.00 |
| 4 | 0.02 |
| 5 | 0.12 |
| 6 | 0.28 |
| 7 | 0.48 |
| 8 | 0.86 |
| 9 | 1.00 |
| 10 | 0.98 |
| 11 | 0.77 |

TABLE 6 pH-stability profile (residual activity after 2 hours at 37° C.)

| pH | *Actinosynnema mirum* trypsin |
|---|---|
| 2.0 | 0.00 |
| 3.0 | 0.28 |
| 4.0 | 1.00 |
| 5.0 | 1.03 |
| 6.0 | 1.05 |
| 7.0 | 1.03 |
| 8.0 | 1.02 |
| 9.0 | 1.01 |
| 10.0 | 0.95 |
| 11.0 | 0.25 |
| 9.0 and after 2 hours at 5° C. | 1.00 |

TABLE 7

Temperature activity profile at pH 7.0

| Temp (° C.) | *Actinosynnema mirum* trypsin |
|---|---|
| 15 | 0.01 |
| 25 | 0.01 |
| 37 | 0.05 |
| 50 | 0.33 |
| 60 | 1.00 |
| 70 | 0.52 |
| 80 | 0.07 |

Characterization: P1-specificity on Suc-AAPX[SEQ ID NO: 21]-pNA substrates and calculation of the Trypsin ratio The pNA assay was used for obtaining the P1-specificity for the trypsin-like protease from *Actinosynnema mirum* using 10 Suc-AAPX[SEQ ID NO: 21]-pNA substrates at pH 9.0. The activities were also used to calculate the trypsin ratio as defined in WO 2010/112546. The results are shown in Table 8 below. For Table 8, the activity for each Suc-AAPX[SEQ ID NO: 21]-pNA substrate is relative to the activity for the best Suc-AAPX[SEQ ID NO: 21]-pNA substrate (Suc-AAPR[SEQ ID NO: 13]-pNA).

TABLE 8

P1-specificity on Suc-AAPX[SEQ ID NO: 21]-pNA and Trypsin ratio at pH 9.0

| Suc-AAPX [SEQ ID NO: 21]-pNA | *Actinosynnema mirum* trypsin |
|---|---|
| Suc-AAPA [SEQ ID NO: 12]-pNA | 0.00000 |
| Suc-AAPR [SEQ ID NO: 13]-pNA | 1.00000 |
| Suc-AAPD [SEQ ID NO: 14]-pNA | 0.00000 |
| Suc-AAPI [SEQ ID NO: 16]-pNA | 0.00000 |
| Suc-AAPM [SEQ ID NO: 19]-pNA | 0.00005 |
| Suc-AAPV [SEQ ID NO: 20]-pNA | 0.00000 |
| Suc-AAPL [SEQ ID NO: 17]-pNA | 0.00003 |
| Suc-AAPE [SEQ ID NO: 15]-pNA | 0.00000 |
| Suc-AAPK [SEQ ID NO: 18]-pNA | 0.40723 |
| Suc-AAPF [SEQ ID NO: 11]-pNA | 0.00013 (0.0001315) |
| Max of Suc-AAP(R/K) [SEQ ID NO: 22]-pNA | 1.00000 |
| Max of Suc-AAPnon(R/K) [SEQ ID NO: 23]-pNA | 0.00013 (0.0001315) |
| Trypsin ratio | 7600 |

Other Characteristics

The trypsin-like protease from *Actinosynnema mirum* is inhibited by PMSF.

The relative molecular weight as determined by SDS-PAGE was $M_r$=26 kDa.

The N-terminal sequence was determined as: IVGGTRA [SEQ ID NO: 25].

The Intact molecular weight was determined to be Mw=22460.9 Da.

These data indicate that the mature trypsin-like protease from *Actinosynnema mirum* has the following sequence (amino acids 38-261 of SEQ ID NO: 5):

IVGGTRASISEAPWTVYLASSSGSQFCGGTLVKANKVVTAAHCVAGRSAS

STRVVIGREDKQSTAGTVATVSGIWSHPSYRTATSGYDVAVLTLGTSVSG

TYLPLATPSDTALYAAGTNAVAYGWGATCSGCSTSRYLLKVTVPVTSDAT

CKTAYSQYSNTSMVCAGVPAGGKDTCQGDSGGPLVAGGKLIGATSWGNGC

ALPNYPGVYARVAAYYSVLSAQIG

Example 6

Purification and Characterization of Trypsin-Like Endopeptidase from *Kribbella flavida*

Purification Activity Assay:
pNA substrate: Suc-AAPR[SEQ ID NO: 13]-pNA (Bachem L-1720).
Temperature: Room temperature (25° C.)
Assay buffer: 100 mM succinic acid, 100 mM HEPES, 100 mM CHES, 100 mM CABS, 1 mM CaCl$_2$, 150 mM KCl, 0.01% Triton X-100, pH 9.0.

20µl protease (diluted in 0.01% Triton X-100) is dispensed in a microtiter plate well. The assay is started by adding 200µl pNA substrate (50 mg Suc-AAPR[SEQ ID NO: 13]-pNA dissolved in 1.0 ml DMSO and further diluted 90× with Assay buffer). The initial increase in OD$_{405}$ is monitored as a measure of the protease activity.

Characterization Activity Assays:
1) pNA Assay:
pNA substrates: Suc-AAPR[SEQ ID NO: 13]-pNA (Bachem L-1720)
    Suc-AAPF[SEQ ID NO: 11]-pNA (Bachem L-1400)
    Suc-AAPA[SEQ ID NO: 12]-pNA (Bachem L-1775)
    Suc-AAPD[SEQ ID NO: 14]-pNA (Bachem L-1835)
    Suc-AAPE[SEQ ID NO: 15]-pNA (Bachem L-1710)
    Suc-AAPI[SEQ ID NO: 16]-pNA (Bachem L-1790)
    Suc-AAPL[SEQ ID NO: 17]-pNA (Bachem L-1390)
    Suc-AAPK[SEQ ID NO: 18]-pNA (Bachem L-1725)
    Suc-AAPM[SEQ ID NO: 19]-pNA (Bachem L-1395)
    Suc-AAPV[SEQ ID NO: 20]-pNA (Bachem L-1770)
Temperature: Room temperature (25° C.)
Assay buffers: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease (diluted in 0.01% Triton X-100) is mixed with 100 µl assay buffer. The assay is started by adding 100 µl pNA substrate (50 mg dissolved in 1.0 ml DMSO and further diluted 45× with 0.01% Triton X-100). The initial increase in OD$_{405}$ is monitored as a measure of the protease activity.

2) Protazyme AK Assay:
Substrate: Protazyme AK tablet (cross-linked and dyed casein; from Megazyme)
Temperature: Controlled (assay temperature).
Assay buffers: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.

A Protazyme AK tablet is suspended in 2.0 ml 0.01% Triton X-100 by gentle stirring. 500 µl of this suspension and 500µl assay buffer are mixed in an Eppendorf tube and placed on ice. 20µl protease sample (diluted in 0.01% Triton X-100) is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200µl supernatant is transferred to a microtiter plate. $OD_{650}$ is read as a measure of protease activity. A buffer blank is included in the assay (instead of enzyme).

Purification of the Trypsin-like Protease from Strain THFF0037

THFF0037 is a Bacillus subtilis strain constructed to express to the culture medium the mature trypsin-like protease from Kribbella flavida, the amino acid sequence of which is shown as SEQ ID NO: 6 of the present application.

The THFF0037 culture broth was centrifuged (20000×g, 20 min) and the supernatants were carefully decanted from the precipitates. The combined supernatants were filtered through a Nalgene 0.2 µm filtration unit in order to remove the rest of the Bacillus host cells. Solid ammonium sulphate was added to the 0.2 µm filtrate to 1.5M final $(NH_4)_2SO_4$ concentration. The filtrate was mixed gently with a magnetic stirrer during the $(NH_4)_2SO_4$ addition and the stirring was continued for 30 minutes after the addition to bring the system in equilibrium. Then the solution was applied to a Phenyl Toyopearl 650S column (TosoHaas) equilibrated in 100 mM $H_3BO_3$, 10 mM MES, 2 mM $CaCl_2$, 1.5M $(NH_4)_2SO_4$, pH 6. After washing the column extensively with the equilibration buffer, the trypsin-like protease was eluted with a linear $(NH_4)_2SO_4$ gradient (1.5-->0M) in the same buffer. Fractions from the column were analysed for trypsin-like protease activity (Purification activity assay) and fractions forming the major activity peak were pooled. The pool from the Phenyl Toyopearl column was transferred to 50 mM $H_3BO_3$, 5 mM MES, 1 mM $CaCl_2$, pH 6 on a G25 sephadex column (GE Healthcare) and the pH was adjusted to pH 4.5 with 20% $CH_3COOH$. The pH adjusted solution was applied to an SOURCE S column (GE Healthcare) equilibrated in 10 mM $CH_3COOH/NaOH$, 1 mM $CaCl_2$, pH 4.5. After washing the column extensively with the equilibration buffer, the protease was eluted with a linear NaCl gradient (0-->0.5M) in the same buffer. Fractions from the column were analysed for trypsin-like protease activity (Purification activity assay) and fractions forming the activity peak were pooled. The pool from the SOURCES column was applied to a Superdex 75 column (GE Healthcare) equilibrated in 100 mM $H_3BO_3$, 10 mM MES, 2 mM $CaCl_2$, 100 mM NaCl, pH 6. The column was eluted with the same buffer, fractions from the column were analysed for trypsin-like protease activity (Purification activity assay) and active fractions were further analysed by SDS-PAGE. Fractions, which were seen to be at least 90% pure on a coomassie stained SDS-PAGE gel, were pooled and was used for further characterization.

Characterization: ph-activity, pH-stability, and Temperature-activity

The pNA assay was used for the pH-activity profile on Suc-AAPR[SEQ ID NO: 13]-pNA and for the pH-stability profile. For the pH-stability profile the protease was diluted 10× in the assay buffers and incubated for 2 hours at 37° C. After incubation the protease samples were transferred to pH 9, before assay for residual activity, by dilution in the pH 9 Assay buffer. The Protazyme AK assay was used for obtaining the temperature-activity profile at pH 7. The results are shown in Tables 9-11 below. For Table 9, the activities are relative to the optimal pH for the enzyme. For Table 10, the activities are residual activities relative to a sample, which was kept at stable conditions (5° C., pH 9). For Table 11, the activities are relative to the optimal temperature at pH 7 for the enzyme.

TABLE 9 pH-activity profile

| pH | Kribbella flavida trypsin |
|---|---|
| 2 | 0.00 |
| 3 | 0.00 |
| 4 | 0.01 |
| 5 | 0.07 |
| 6 | 0.29 |
| 7 | 0.60 |
| 8 | 0.83 |
| 9 | 0.93 |
| 10 | 1.00 |
| 11 | 0.90 |

TABLE 10 pH-stability profile (residual activity after 2 hours at 37° C.)

| pH | Kribbella flavida trypsin |
|---|---|
| 2.0 | 0.19 |
| 3.0 | 0.37 |
| 4.0 | 0.66 |
| 5.0 | 0.91 |
| 6.0 | 0.96 |
| 7.0 | 0.95 |
| 8.0 | 0.95 |
| 9.0 | 0.86 |
| 10.0 | 0.48 |
| 11.0 | 0.01 |
| 9.0 and after 2 hours at 5° C. | 1.00 |

TABLE 11

Temperature activity profile at pH 7.0

| Temp (° C.) | Kribbella flavida trypsin |
|---|---|
| 15 | 0.04 |
| 25 | 0.10 |
| 37 | 0.30 |
| 50 | 1.00 |
| 60 | 0.27 |
| 70 | 0.12 |

Characterization: P1-specificity on Suc-AAPX[SEQ ID NO: 21]-pNA substrates and calculation of the Trypsin ratio The pNA assay was used for obtaining the P1-specificity for the trypsin-like protease from Actinosynnema mirum using 10 Suc-AAPX[SEQ ID NO: 21]-pNA substrates at pH 9.0. The activities were also used to calculate the trypsin ratio as defined in WO 2010/112546. The results are shown in Table 12 below. For Table 8, the activity for each Suc-AAPX[SEQ ID NO: 21]-pNA substrate is relative to the activity for the best Suc-AAPX[SEQ ID NO: 21]-pNA substrate (Suc-AAPR[SEQ ID NO: 13]-pNA).

TABLE 12

P1-specificity on Suc-AAPX[SEQ ID NO: 21]-pNA and Trypsin ratio at pH 9.0

| Suc-AAPX<br>[SEQ ID NO: 21]-pNA | Kribbella flavida<br>trypsin |
|---|---|
| Suc-AAPA<br>[SEQ ID NO: 12]-pNA | 0.00001 |
| Suc-AAPR<br>[SEQ ID NO: 13]-pNA | 1.00000 |
| Suc-AAPD<br>[SEQ ID NO: 14]-pNA | 0.00000 |
| Suc-AAPI<br>[SEQ ID NO: 16]-pNA | 0.00002 |
| Suc-AAPM<br>[SEQ ID NO: 19]-pNA | 0.00004 |
| Suc-AAPV<br>[SEQ ID NO: 20]-pNA | 0.00000 |
| Suc-AAPL<br>[SEQ ID NO: 17]-pNA | 0.00002 |
| Suc-AAPE<br>[SEQ ID NO: 15]-pNA | 0.00001 |
| Suc-AAPK<br>[SEQ ID NO: 18]-pNA | 0.56906 |
| Suc-AAPF<br>[SEQ ID NO: 11]-pNA | 0.00005<br>(0.0000477) |
| Max of Suc-AAP(R/K)<br>[SEQ ID NO: 22]-pNA | 1.00000 |
| Max of Suc-AAPnon(R/K)<br>[SEQ ID NO: 23]-pNA | 0.00005<br>(0.0000477) |
| Trypsin ratio | 21000 |

Other Characteristics

The trypsin-like protease from *Kribbella flavida* is inhibited by EDTA.

The relative molecular weight as determined by SDS-PAGE was $M_r=26$ kDa.

The N-terminal sequence was determined as: IVGGSL [SEQ ID NO: 26].

The Intact molecular weight was determined to be Mw=23169.0 Da.

These data indicate that the mature trypsin-like protease from *Kribbella flavida* has the following sequence (amino acids 40-266 of SEQ ID NO: 6):

IVGGSLASTAQAPWAIALNNSQSPSPSGQWCGATLVKANKIVTAAHCVTK

ARSTYTAIQGRDSLSSTTGRTSKIASIWKDPQYGRAPGHDVAVLTLATPF

TGVPTLPLETSLAADAVGAQPTVYGWGNTEGTGPADRFQKVLVPVLGDAY

CGQVYANYDYVANGEICAGYKEGGKDSCQGDSGGPLVLNGRLFGVVSWGI

GCADAGNPGVYAEVATYAAALTAQINS

The calculated molecular weight from this mature sequence was 23168.7 Da.

Example 7

Hydrolysis of Whey Protein Concentrate and of Alpha Lactalbumin with Trypsin-like Proteases from *Actinosynnema mirum* and *Kribbella flavida*

Materials:

Whey protein concentrate (WPC), 80% dry matter protein, Lacprodan 80, Arla Foods Ingredients, DK Alpha lactalbumin (ALA), 97% dry matter protein, Davisco Foods International, MN, US CaCl$_2$ anhydrous, Merck art 2387

NaOH, Prolabo 31627.368

Hydrolysis Assay: 1 g Alpha-lactalbumin dissolved in 17.6 ml of 5 mM CaCl$_2$ or 1.2 g Lacprodan 80 in 17.4 ml of 5 mM CaCl$_2$ were produced to obtain a final protein concentration of 5%.

Samples were heated to 55° C. or 50° C. and pH was adjusted to 7.5. The NaOH volume consumed for pH adjustment was recorded. Enzyme was added and pH titration was carried out on Titralab 856 (Radiometer) for 120 min. NaOH consumption was monitored and converted into % DH.

Degree of Hydrolysis (DH):

Degree of hydrolysis of the suspension was measured by pH stat as described in Adler-Nissen, J. 1986, Enzymatic Hydrolysis of Food Proteins, Chapter 6.

Degree of Hydrolysis (DH) defined as the percentage of peptide bonds cleaved can be monitored with pH-stat technique: $DH=h/h_{tot} \times 100$ h: number of peptide bonds cleaved, proportional to the amount of base consumed during the reaction.

$h_{tot}$: number of peptide bonds in a protein calculated from the amino acid composition.

$h_{tot}$ for ALA=8.16 and $h_{tot}$ for WPC=8.8

$h = B \times Nb \times 1/\alpha \times 1/Mp$

B=base consumption (ml)

Nb=Normality of the base (0.25 N)

$1/\alpha$=average degree of dissociation of the α-NH$_2$ groups

Mp=Protein mass (g), (N×Kjeldahl factor)

Endopeptidases Used:

| Enzyme | Conc. (mg/ml) |
|---|---|
| Trypsin-like protease from *Actinosynnema mirum* | 0.69 mg/ml |
| Trypsin-like protease from *Kribella flavida* | 0.38 mg/ml |
| Trypsin-like protease from *Fusarium oxysporum* | 8.0 mg/ml |
| Trypsin, chromatographically purified from Porcine trypsin (PTN 6.0S) | 9.5 mg/ml |
| Chymotrypsin-like protease from *Nocardiopsis* sp. NRRL 18262 | 8.8 mg/ml |
| Porcine Pancreas Trypsin Novo 6.0S, PTN | 200 mg/g |

For amino acid sequences of the trypsin-like protease from *Fusarium oxysporum* and the chymotrypsin-like protease from *Nocardiopsis* sp. NRRL 18262, see WO 2010/112546.

Data:

ALA Hydrolysed with Trypsin-Like Enzymes:

| | Dosage | DH (120 min) |
|---|---|---|
| Trypsin-like protease from *Actinosynnema mirum* | 2 mg enzyme protein/g protein | 6.5 |
| Trypsin-like protease from *Kribella flavida* | 2 mg enzyme protein/g protein | 7.9 |
| Trypsin-like protease from *Fusarium oxysporum* | 2 mg enzyme protein/g protein | 4.8 |
| Trypsin, chromatographically purified from Porcine trypsin, PTN 6.0S | 2 mg enzyme protein/g protein | 9.0 |

ALA Hydrolysed with Trypsin-Like Enzymes+Chymotrypsin-Like:

|  | Dosage | DH (120 min) |
|---|---|---|
| Trypsin-like protease from *Actinosynnema mirum* + chymotrypsin-like from *Nocardiopsis* | 1.8 + 0.2 mg enzyme protein/g protein | 11.9 |
| Trypsin-like protease from *Kribella flavida* + chymotrypsin-like from *Nocardiopsis* | 1.8 + 0.2 mg enzyme protein/g protein | 8.9 |
| Trypsin-like protease from *Fusarium oxysporum* + chymotrypsin-like from *Nocardiopsis* | 1.8 + 0.2 mg enzyme protein/g protein | 8.4 |
| Porcine trypsin (PTN 6.0S) | 2 mg enzyme protein/g protein | 13.3 |

WPC Hydrolysed with Trypsin-Like Enzymes+Chymotrypsin-Like:

|  | Dosage | DH (120 min) |
|---|---|---|
| Trypsin-like protease from *Actinosynnema mirum* + chymotrypsin-like from *Nocardiopsis* | 1.8 + 0.2 mg enzyme protein/g protein | 10.9 |
| Trypsin-like protease from *Fusarium oxysporum* + chymotrypsin-like from *Nocardiopsis* | 1.8 + 0.2 mg enzyme protein/g protein | 9.9 |
| Porcine trypsin (PTN 6.0S) | 2 mg enzyme protein/g protein | 10.1 |

Deposit of Biological Material

The following biological material has been deposited under the terms of the Budapest Treaty with the Deutsche Sammlung von Mikroorganismen and Zellkulturen GmbH (DSM), Mascheroder Weg 1 B, D-38124 Braunschweig, Germany, and given the following accession number:

| Deposit: | Accession Number: | Date of Deposit: |
|---|---|---|
| *Escherichia coli* NN059278 | DSM 23706 | Jun. 18, 2010 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several embodiments of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method of producing a polypeptide having endopeptidase activity, comprising:
   (a) providing a recombinant host cell comprising a polynucleotide encoding a polypeptide having endopeptidase activity operably linked to one or more heterologous control sequences that direct expression of the polypeptide, wherein the polypeptide comprises an amino acid sequence that has at least 90% sequence identity to the amino acid sequence of SEQ ID NO: 2;
   (b) cultivating the recombinant host cell in a culture medium under conditions conducive for production of the polypeptide; and
   (c) recovering the polypeptide from the culture medium.

2. A method of making a protein hydrolysate comprising:
   (a) providing a solution comprising protein to be hydrolyzed;
   (b) adding to said solution an isolated polypeptide having endopeptidase activity, and wherein the polypeptide comprises an amino acid sequence that has at least 90% sequence identity to the amino acid sequence of SEQ ID NO: 2; and
   (c) obtaining the protein hydrolysate.

3. The method of claim 2, wherein the protein to he hydrolyzed is food protein.

4. The method of claim 1, wherein the polypeptide having endopeptidase activity has at least 95% sequence identity to the sequence of SEQ ID NO: 2.

5. The method of claim 1, wherein the polypeptide having endopeptidase activity has at least 97% sequence identity to the sequence of SEQ ID NO: 2.

6. The method of claim 1, wherein the polypeptide having endopeptidase activity has at least 98% sequence identity to the sequence of SEQ ID NO: 2.

7. The method of claim 1, wherein the polypeptide having endopeptidase activity has at least 99% sequence identity to the sequence of SEQ ID NO: 2.

8. The method of claim 1, wherein the polypeptide having endopeptidase activity comprises or consists of the amino acid sequence of SEQ ID NO: 2.

9. The method of claim 3, wherein the solution comprising food protein is a solution comprising protein material from a plant and/or an animal.

10. The method of claim 2, wherein the polypeptide having endopeptidase activity has at least 95% sequence identity to the sequence of SEQ ID NO: 2.

11. The method of claim 2, wherein the polypeptide having endopeptidase activity has at least 97% sequence identity to the sequence of SEQ ID NO: 2.

12. The method of claim 2, wherein the polypeptide having endopeptidase activity has at least 98% sequence identity to the sequence of SEQ ID NO: 2.

13. The method of claim 2 wherein the polypeptide having endopeptidase activity has at least 99% sequence identity to the sequence of SEQ ID NO: 2.

14. The method of claim 2 wherein the polypeptide having endopeptidase activity comprises or consists of the amino acid sequence of SEQ ID NO: 2.

* * * * *

SEQUENCE LISTING

```
<160> NUMBER OF SEQ ID NOS: 9

<210> SEQ ID NO 1
<211> LENGTH: 675
<212> TYPE: DNA
<213> ORGANISM: Kutzneria albida

<400> SEQUENCE: 1
atcgtcggcg gtacgaaggc cagtacctcg acctacccgt tcgtggtctt cctgactgac      60
agcaccggtt tccagttctg cggtggcacg ctggtcaagc cgaacaaggt ggtcacggcg     120
gcgcactgca ccgtcggtga gtccgcggcc aacatccgcg ttgtcgccgg tcgcgacgac     180
aagcagagca ccgccggcac tgtctcgaag gtcagcaaga tctggatcca cccgagttac     240
caggacgcca ccaagggcag cgacgtgtcg gtgctgaccc tgtcgaccag cctgacccag     300
ttcacgccgt tgccgctggc tgccaccact gacaccgcgc tgtacaagga gggcaccgcc     360
gcgaccatcc tcggctgggg tgacaccacc gagggcgggt cggcctctcg gtacctgctc     420
aaggcgacag tgccgctgac cagcgacgcc acctgcaaga aggcgtacgg cgagtacagt     480
tccaccgcga tggtctgtgc cggatacccg cagggtggca cggacacctg ccaggcgac     540 tccggcggtc cgctcgtcgc cggcaacaag ctgatcggca tcacctcgtg gggccagggc     600
tgcgccgagg ccggttatcc aggcgtctac acccgggtcg ccacctacag ttcgctgatc     660
acccagcagc tcggc                                                      675
```

<210> SEQ ID NO 2
<211> LENGTH: 225
<212> TYPE: PRT
<213> ORGANISM: Kutzneria albida

<400> SEQUENCE: 2

```
Ile Val Gly Gly Thr Lys Ala Ser Thr Ser Thr Tyr Pro Phe Val Val
  1               5                  10                  15

Phe Leu Thr Asp Ser Thr Gly Phe Gln Phe Cys Gly Gly Thr Leu Val
             20                  25                  30

Lys Pro Asn Lys Val Val Thr Ala Ala His Cys Thr Val Gly Glu Ser
         35                  40                  45

Ala Ala Asn Ile Arg Val Val Ala Gly Arg Asp Asp Lys Gln Ser Thr
     50                  55                  60

Ala Gly Thr Val Ser Lys Val Ser Lys Ile Trp Ile His Pro Ser Tyr
 65                  70                  75                  80

Gln Asp Ala Thr Lys Gly Ser Asp Val Ser Val Leu Thr Leu Ser Thr
                 85                  90                  95

Ser Leu Thr Gln Phe Thr Pro Leu Pro Leu Ala Ala Thr Thr Asp Thr
            100                 105                 110

Ala Leu Tyr Lys Glu Gly Thr Ala Ala Thr Ile Leu Gly Trp Gly Asp
        115                 120                 125

Thr Thr Glu Gly Gly Ser Ala Ser Arg Tyr Leu Leu Lys Ala Thr Val
    130                 135                 140

Pro Leu Thr Ser Asp Ala Thr Cys Lys Lys Ala Tyr Gly Glu Tyr Ser
145                 150                 155                 160

Ser Thr Ala Met Val Cys Ala Gly Tyr Pro Gln Gly Gly Thr Asp Thr
                165                 170                 175

Cys Gln Gly Asp Ser Gly Gly Pro Leu Val Ala Gly Asn Lys Leu Ile
            180                 185                 190

Gly Ile Thr Ser Trp Gly Gln Gly Cys Ala Glu Ala Gly Tyr Pro Gly
        195                 200                 205

Val Tyr Thr Arg Val Ala Thr Tyr Ser Ser Leu Ile Thr Gln Gln Leu
    210                 215                 220

Gly
225
```

<210> SEQ ID NO 3
<211> LENGTH: 756
<212> TYPE: DNA
<213> ORGANISM: Artificial sequence
<220> FEATURE:
<223> OTHER INFORMATION: Synthetic construct

<400> SEQUENCE: 3

```
atgaagaaac cgttggggaa aattgtcgca agcaccgcac tactcatttc tgttgctttt      60
agttcatcga tcgcatcggc tatcgttggt ggcactaaag cttcaacttc aacataccca     120
ttcgttgttt ttcttactga ctctacaggt ttccagtttt gtggtggcac acttgttaaa     180
ccaaacaaag ttgttactgc agcgcattgc acagttggcg agtcagctgc aaacatccgc     240
gttgttgcgg tcgcgacga caaacagtca actgctggca ctgtttctaa gtaagcaaa      300 atctggatcc atccttctta ccaagacgct acaaaaggct cagacgtttc agtacttact     360 cttttctacgt ctcttacgca gttcacacct cttccgcttg cagcaactac ggacacagca     420
ctttacaaag agggaactgc ggcaactatc cttggttggg gtgacacaac tgagggaggc     480
```

```
tctgcttcac gctaccttct taaagcaaca gtacctctta ctagcgacgc tacttgcaag    540
aaagcttacg gtgagtactc ttcaacagcg atggtttgcg caggctatcc tcaaggcgga    600
actgacacgt gccagggcga ctctggtggc cctcttgtag ctggcaacaa gcttatcggc    660
atcacttctt ggggtcaagg ctgtgctgag gctggttacc caggagttta cactcgcgtt    720
gctactattc tagccttat cactcaacag cttggc                              756
```

<210> SEQ ID NO 4
<211> LENGTH: 27
<212> TYPE: PRT
<213> ORGANISM: Bacillus clausii
<400> SEQUENCE: 4

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```

<210> SEQ ID NO 5
<211> LENGTH: 261
<212> TYPE: PRT
<213> ORGANISM: Actinosynnema mirum
<400> SEQUENCE: 5

```
Met Ala Lys Thr Leu Arg Arg Leu Ala Lys Phe Ile Gly Leu Gly Val
1               5                   10                  15

Ala Ala Ala Ala Ile Gly Leu Met Thr Thr Pro Val Ser Ser Ala Ser
            20                  25                  30

Asp Val Thr Pro Phe Ile Val Gly Gly Thr Arg Ala Ser Ile Ser Glu
        35                  40                  45

Ala Pro Trp Thr Val Tyr Leu Ala Ser Ser Gly Ser Gln Phe Cys
    50                  55                  60

Gly Gly Thr Leu Val Lys Ala Asn Lys Val Val Thr Ala Ala His Cys
65                  70                  75                  80

Val Ala Gly Arg Ser Ala Ser Ser Thr Arg Val Val Ile Gly Arg Glu
                85                  90                  95

Asp Lys Gln Ser Thr Ala Gly Thr Val Ala Thr Val Ser Gly Ile Trp
            100                 105                 110

Ser His Pro Ser Tyr Arg Thr Ala Thr Ser Gly Tyr Asp Val Ala Val
        115                 120                 125

Leu Thr Leu Gly Thr Ser Val Ser Gly Thr Tyr Leu Pro Leu Ala Thr
    130                 135                 140

Pro Ser Asp Thr Ala Leu Tyr Ala Ala Gly Thr Asn Ala Val Ala Tyr
145                 150                 155                 160

Gly Trp Gly Ala Thr Cys Ser Gly Cys Ser Thr Ser Arg Tyr Leu Leu
                165                 170                 175

Lys Val Thr Val Pro Val Thr Ser Asp Ala Thr Cys Lys Thr Ala Tyr
            180                 185                 190

Ser Gln Tyr Ser Asn Thr Ser Met Val Cys Ala Gly Val Pro Ala Gly
        195                 200                 205

Gly Lys Asp Thr Cys Gln Gly Asp Ser Gly Pro Leu Val Ala Gly
    210                 215                 220

Gly Lys Leu Ile Gly Ala Thr Ser Trp Gly Asn Gly Cys Ala Leu Pro
225                 230                 235                 240

Asn Tyr Pro Gly Val Tyr Ala Arg Val Ala Ala Tyr Tyr Ser Val Leu
                245                 250                 255
```

```
Ser Ala Gln Ile Gly
            260

<210> SEQ ID NO 6
<211> LENGTH: 266
<212> TYPE: PRT
<213> ORGANISM: Kribbella flavida

<400> SEQUENCE: 6

Met Thr Gly Lys Leu Thr Phe Ala Arg Ala Ala Leu Ala Ala Ala Val
1               5                   10                  15

Val Ala Leu Ala Ser Thr Gly Ala Val Gly Ala Gln Ala Lys Pro
            20                  25                  30

Pro Ala Pro Pro Val Thr Asn Ile Val Gly Gly Ser Leu Ala Ser Thr
            35                  40                  45

Ala Gln Ala Pro Trp Ala Ile Ala Leu Asn Asn Ser Gln Ser Pro Ser
        50                  55                  60

Pro Ser Gly Gln Trp Cys Gly Ala Thr Leu Val Lys Ala Asn Lys Ile
65                  70                  75                  80

Val Thr Ala Ala His Cys Val Thr Lys Ala Arg Ser Thr Tyr Thr Ala
                85                  90                  95

Ile Gln Gly Arg Asp Ser Leu Ser Ser Thr Thr Gly Arg Thr Ser Lys
            100                 105                 110

Ile Ala Ser Ile Trp Lys Asp Pro Gln Tyr Gly Arg Ala Pro Gly His
            115                 120                 125

Asp Val Ala Val Leu Thr Leu Ala Thr Pro Phe Thr Gly Val Pro Thr
        130                 135                 140

Leu Pro Leu Glu Thr Ser Leu Ala Ala Asp Ala Val Gly Ala Gln Pro
145                 150                 155                 160

Thr Val Tyr Gly Trp Gly Asn Thr Glu Gly Thr Gly Pro Ala Asp Arg
                165                 170                 175

Phe Gln Lys Val Leu Val Pro Val Leu Gly Asp Ala Tyr Cys Gly Gln
            180                 185                 190

Val Tyr Ala Asn Tyr Asp Tyr Val Ala Asn Gly Glu Ile Cys Ala Gly
            195                 200                 205

Tyr Lys Glu Gly Gly Lys Asp Ser Cys Gln Gly Asp Ser Gly Gly Pro
        210                 215                 220

Leu Val Leu Asn Gly Arg Leu Phe Gly Val Val Ser Trp Gly Ile Gly
225                 230                 235                 240

Cys Ala Asp Ala Gly Asn Pro Gly Val Tyr Ala Glu Val Ala Thr Tyr
                245                 250                 255

Ala Ala Ala Leu Thr Ala Gln Ile Asn Ser
            260                 265

<210> SEQ ID NO 7
<211> LENGTH: 188
<212> TYPE: PRT
<213> ORGANISM: Nocardiopsis sp. NRRL 18262

<400> SEQUENCE: 7

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45
```

```
Arg Gly Val Phe Glu Gln Ser Val Phe Pro Gly Asn Asp Ala Ala Phe
 50                  55                  60

Val Arg Gly Thr Ser Asn Phe Thr Leu Thr Asn Leu Val Ser Arg Tyr
 65                  70                  75                  80

Asn Thr Gly Gly Tyr Ala Thr Val Ala Gly His Asn Gln Ala Pro Ile
                 85                  90                  95

Gly Ser Ser Val Cys Arg Ser Gly Ser Thr Thr Gly Trp His Cys Gly
                100                 105                 110

Thr Ile Gln Ala Arg Gly Gln Ser Val Ser Tyr Pro Glu Gly Thr Val
                115                 120                 125

Thr Asn Met Thr Arg Thr Thr Val Cys Ala Glu Pro Gly Asp Ser Gly
        130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
                180                 185

<210> SEQ ID NO 8
<211> LENGTH: 374
<212> TYPE: PRT
<213> ORGANISM: Metarhizium anisopliae

<400> SEQUENCE: 8

Met Glu Leu Thr Lys Phe Leu Ala Leu Leu Ala Val Ile Leu Pro Val
 1               5                  10                  15

Ala Tyr Gly Ala Pro Thr Gln Ala Ala Ser Leu His Pro Gln Ile Leu
                 20                  25                  30

Glu Ala Met Lys Arg Asp Leu Gly Leu Asn Ala Glu Gln Ala Thr Val
            35                  40                  45

Arg Val Ala Arg Glu Ile His Ala Thr Asp Val Ile Glu Gln Leu Arg
 50                  55                  60

Ser Ser Val Ala Phe Ala Gly Ala Trp Ile Asp Ala Asp Val Leu Tyr
 65                  70                  75                  80

Ile Gly Ile Thr Asp Gln Ala Leu Ala Asp Glu Val Thr Ala Ala Gly
                 85                  90                  95

Ala Thr Pro Ile Val Met Thr Asn Ser Leu Ser Lys Leu Glu Lys Ala
                100                 105                 110

Lys Glu Asp Leu Asp Lys Ile Phe Ile Gly Arg Ala Asn Thr Leu Glu
            115                 120                 125

Thr Ser Ser Asp Thr Ser Ser Gly Ile Ala Ser Tyr Phe Val Asp Val
130                 135                 140

Ala Ala Asn Lys Leu Val Ile Glu Ala Leu Ala Asp Ser His Gly His
145                 150                 155                 160

Ala Glu Gln Leu Ala Ala Gln Val Gly Leu Thr Ser Glu Phe Glu Val
                165                 170                 175

Arg Thr Val Glu Thr Met Pro Thr Thr Met Ala Thr Val Gln Gly Gly
            180                 185                 190

Asp Val Tyr Tyr Ile Asn Arg Ser Ser Arg Cys Ser Ile Gly Phe Ala
                195                 200                 205

Val Thr Thr Gly Phe Val Ser Ala Gly His Cys Gly Gly Ser Gly Ala
            210                 215                 220

Ser Ala Thr Thr Ser Ser Gly Glu Ala Leu Gly Thr Phe Ser Gly Ser
```

```
225                 230                 235                 240
Val Phe Pro Gly Ser Ala Asp Met Ala Tyr Val Arg Thr Val Ser Gly
                245                 250                 255

Thr Val Leu Arg Gly Tyr Ile Asn Gly Tyr Gly Gln Gly Ser Phe Pro
                260                 265                 270

Val Ser Gly Ser Ser Glu Ala Ala Val Gly Ala Ser Ile Cys Arg Ser
                275                 280                 285

Gly Ser Thr Thr Gln Val His Cys Gly Thr Ile Gly Ala Lys Gly Ala
            290                 295                 300

Thr Val Asn Tyr Pro Gln Gly Ala Val Ser Gly Leu Thr Arg Thr Ser
305                 310                 315                 320

Val Cys Ala Glu Pro Gly Asp Ser Gly Gly Ser Phe Tyr Ser Gly Ser
                325                 330                 335

Gln Ala Gln Gly Val Thr Ser Gly Gly Ser Gly Asp Cys Ser Arg Gly
                340                 345                 350

Gly Thr Thr Tyr Phe Gln Pro Val Asn Arg Ile Leu Gln Thr Tyr Gly
                355                 360                 365

Leu Thr Leu Val Thr Ala
    370

<210> SEQ ID NO 9
<211> LENGTH: 375
<212> TYPE: PRT
<213> ORGANISM: Brachysporiella gayana

<400> SEQUENCE: 9

Met Glu Leu Thr Ser Leu Ile Ala Ala Leu Ala Val Ile Leu Pro Ile
1               5                   10                  15

Ala Tyr Gly Val Pro Met Asp Ala Thr Thr Asn Leu Ser Pro Lys Val
            20                  25                  30

Leu Ala Ala Met Lys Arg Asp Leu Gly Leu Asp Ala Arg Glu Ala Thr
        35                  40                  45

Ala Arg Val Thr Phe Glu Arg Arg Ala Gly Asp Val Ile Glu Glu Leu
    50                  55                  60

Arg Ser Ser Leu Gly Asp Ser Phe Ala Gly Ala Trp Val Thr Asp Gly
65                  70                  75                  80

Lys Val Ile Asn Ile Gly Val Thr Asp Gln Ala Leu Val Ser Lys Val
                85                  90                  95

Lys Glu Ala Gly Ala Glu Pro Met Val Met Lys Asn Ser Leu Gly Lys
            100                 105                 110

Leu Gln Glu Ala Lys Lys Lys Leu Asp Gln Ile Ile Lys Glu Lys Pro
        115                 120                 125

Lys Thr Leu Ser Thr Ser Gly Lys Pro Gly Ile Ala Thr Tyr Tyr Val
    130                 135                 140

Asp Ile Glu Thr Asn Lys Leu Ile Ile Thr Ala Leu Ser Thr Ser Ile
145                 150                 155                 160

Thr Gln Ala Glu Asp Leu Ala Lys Glu Val Gly Leu Ser Glu Ser Glu
                165                 170                 175

Phe Glu Val Arg Lys Thr Glu Lys Met Pro Ser Pro Phe Ile Leu Gly
            180                 185                 190

Gly Asp Pro Phe Val Ile Asn Asn Ser Ala Val Cys Ser Val Gly Phe
        195                 200                 205

Ala Val Ser Gly Gly Phe Val Ser Ala Gly His Cys Gly Gly Gln Gly
    210                 215                 220
```

-continued

```
Ser Pro Val Thr Tyr Ile Asp Gly Gly Ala Leu Gly Thr Ile Glu Gly
225                 230                 235                 240

Ser Val Phe Pro Gly Asp Ala Asp Met Ser Phe Ile Arg Ala Val Asp
                245                 250                 255

Gly Thr Asp Leu Pro Gly Ile Val Gly Thr Tyr Gly Asn Gly Asp Gln
            260                 265                 270

Pro Ile Phe Gly Ser Asn Val Ala Pro Ile Gly Ser Gly Val Cys Arg
            275                 280                 285

Ser Gly Thr Thr Thr Gly Tyr His Cys Gly Gln Leu Asp Ala Tyr Asp
        290                 295                 300

Val Thr Val Asn Tyr Asp Val Gly Pro Val Phe Gly Leu Thr Met Thr
305                 310                 315                 320

Ser Ala Cys Ala Glu Pro Gly Asp Ser Gly Gly Ser Phe Phe Ala Gly
                325                 330                 335

Asp Gln Ala Gln Gly Val Thr Ser Gly Gly Ser Gly Asp Cys Thr Ser
            340                 345                 350

Gly Gly Gln Thr Phe Phe Gln Pro Val Asn Glu Ile Leu Glu Thr Tyr
        355                 360                 365

Gly Leu Ser Leu Thr Thr Ala
    370                 375
```